United States Patent
Sun et al.

(10) Patent No.: US 11,168,327 B2
(45) Date of Patent: Nov. 9, 2021

(54) STEAP2 INHIBITORS FOR THE TREATMENT OF LIVER CANCERS

(71) Applicant: Research Development Foundation, Carson City, NV (US)

(72) Inventors: Luzhe Sun, San Antonio, TX (US); Carla Zeballos Torrez, San Antonio, TX (US); Xiang Gu, San Antonio, TX (US); Francisco Cigarroa, San Antonio, TX (US)

(73) Assignee: Research Development Foundation, Carson City, NV (US)

( * ) Notice: Subject to any disclaimer, the term of this patent is extended or adjusted under 35 U.S.C. 154(b) by 0 days.

(21) Appl. No.: 16/481,950

(22) PCT Filed: Jan. 31, 2018

(86) PCT No.: PCT/US2018/016212
§ 371 (c)(1),
(2) Date: Jul. 30, 2019

(87) PCT Pub. No.: WO2018/144587
PCT Pub. Date: Aug. 9, 2018

(65) Prior Publication Data
US 2019/0352646 A1   Nov. 21, 2019

Related U.S. Application Data

(60) Provisional application No. 62/452,695, filed on Jan. 31, 2017.

(51) Int. Cl.
*A61K 48/00* (2006.01)
*C12N 15/11* (2006.01)
(Continued)

(52) U.S. Cl.
CPC .......... *C12N 15/1137* (2013.01); *A61K 9/127* (2013.01); *A61K 9/14* (2013.01); *A61K 31/713* (2013.01); *A61K 31/7105* (2013.01); *A61P 35/00* (2018.01); *C07K 16/40* (2013.01); *A61K 45/06* (2013.01)

(58) Field of Classification Search
CPC .. A61K 31/713; A61K 31/7105; A61K 45/06; A61K 9/14; A61K 9/127; C12N 15/1135; C12N 15/1137; C12N 2310/14
See application file for complete search history.

(56) References Cited

U.S. PATENT DOCUMENTS

2016/0243225 A1   8/2016   Ioffe et al.

FOREIGN PATENT DOCUMENTS

WO   WO 2005/079490   9/2005

OTHER PUBLICATIONS

Scanlon KJ (Current Pharmaceutical Biotechnology, 2004 vol. 5:415-420).*

(Continued)

*Primary Examiner* — Terra C Gibbs
(74) *Attorney, Agent, or Firm* — Parker Highlander PLLC

(57) ABSTRACT

Provided are methods for the diagnosis and treatment of liver cancers such as hepatocellular carcinoma (HCC). In some aspects, the methods comprise administering an inhibitor of STEAP2 to a subject to treat a liver cancer. In some embodiments, a STEAP2 targeting siRNA or antibody is administered to a subject to treat HCC.

19 Claims, 16 Drawing Sheets

Specification includes a Sequence Listing.

(51) Int. Cl.

| | |
|---|---|
| C07H 21/02 | (2006.01) |
| C07H 21/04 | (2006.01) |
| C12N 15/113 | (2010.01) |
| A61P 35/00 | (2006.01) |
| A61K 9/127 | (2006.01) |
| A61K 9/14 | (2006.01) |
| A61K 31/7105 | (2006.01) |
| A61K 31/713 | (2006.01) |
| C07K 16/40 | (2006.01) |
| A61K 45/06 | (2006.01) |

(56) References Cited

OTHER PUBLICATIONS

Begum et al., "Differential display and integrin alpha 6 messenger RNA overexpression in hepatocellular carcinoma," *Hepatology*, 22(5):1447-1455, 1995.

Bouamar et al., "High iron or high fat diet show similar effects in inducing hepatocellular carcinoma in a mouse model," AACR Annual Meeting Abstract 96, 2019.

Gomes et al., "STEAP proteins: from structure to applications in cancer therapy," *Mol Cancer Res.*, 10(5):573-587, 2012.

Hass et al., "Gene-expression Analysis Identifies Specific Patterns of Dysregulated Molecular Pathways and Genetic Subgroups of Human Hepatocellular Carcinoma," *Anticancr Res.*, 36(10):5087-5095, 2016.

Iizuka et al., "Different molecular pathways determining extrahepatic and intrahepatic recurrences of hepatocellular carcinoma," *Oncol. Rep.*, 16(5):1137-1142, 2006.

Ikawa-Yoshida et al., "Hepatocellular carcinoma in a mouse model fed a choline-deficient, L-amino acid-defined, high-fat diet," *International Journal of Experimental Pathology*, 98:221-233, 2017.

Kew, "Hepatic iron overload and hepatocellular carcinoma," *Liver Cancer*, 3:31-40, 2014.

Kikkawa et al., "Laminin alpha 5 mediates ectopic adhesion of hepatocellular carcinoma through integrins and/or Lutheran/basal cell adhesion molecule," *Exp. Cell Res.*, 314(14):2579-2590, 2008.

Korkmaz et al., "Molecular cloning and characterization of STAMP1, a highly prostate specific six transmembrane protein that is overexpressed in prostate cancer," *J Biol Chem*, 277:36689-36696, 2002.

Lafaro and Pawlik, "Fibrolamellar hepatocellular carcinoma: current clinical perspectives," *Journal of Hepatocellular Carcinoma*, 2:151-157, 2015.

Llovet et al., "The Barcelona approach: diagnosis, staging, and treatment of hepatocellular carcinoma." Liver Transpl.;10(2 Suppl 1):S115-20. Review, Feb. 2004.

Lu et al., "Laminin and its alpha 6 integrin receptor in the regulation of human hepatocellular carcinoma cell phenotypes," *Zhonghua Zhong Liu Za Zhi*, 25(1):31-35, 2003.

Lu et al., "Mechanism of enhanced invasiveness of human hepatocellular carcinoma by integrin alpha 6 beta 1," *Zhonghua Zhong Liu Za Zhi*, 22(4):287-289, 2000.

Lv et al., "RNA interference targeting human integrin α6 suppresses the metastasis potential of hepatocellular carcinoma cells," *European Journal of Medical Research*, 18:52, 2013.

PCT International Preliminary Report on Patentability issued in International Application No. PCT/US2018/016212, dated Aug. 15, 2019.

PCT International Search Report and Written Opinion issued in International Application No. PCT/US2018/016212, dated May 29, 2018.

Porkka et al., "Cloning and characterization of a novel six-transmembrane protein STEAP2, expressed in normal and malignant prostate," *Lab Invest*, 82(11):1573-1582, 2002.

Rohr-Udilova et al., "Deviations of the immune cell landscape between healthy liver and hepatocellular carcinoma," *Scientific Reports*, 8(1):6220, 2018.

Simonetti et al., "Treatment of hepatocellular carcinoma: a systematic review of randomized controlled trials," *Ann Oncol.*, 8(2):117-136, 1997.

Song et al., "RNA interference targeting Fas protects mice from fulminant hepatitis," *Nat Med.*, 9(3):347-351, 2003.

Soutschek et al., "Therapeutic silencing of an endogenous gene by systemic administration of modified siRNAs," *Nature*, 432(7014):173-178, 2004.

Tessitore et al., "MicroRNA expression analysis in high fat diet-induced NAFLD-NASH-HCC progression: study on C57BL/6J mice," *BMC Cancer*, 16:3, 2016.

Volpes et al., "Integrins as differential cell lineage markers of primary liver tumors," *Am J Pathol.*, 142(5):1483-1492, 1993.

Wadhwa et al., "Vectors for RNA interference," *Curr. Opin. Mol. Ther.*, 6(4):367-372, 2004. Abstract only.

Zeballos et al., "The role of six transmembrane epithelial antigen of the prostate 2 in hepatocellular carcinoma," Poster, *HCC Summit*, 2017.

Zeballos et al., "The role of six transmembrane epithelial antigen of the prostate 2 in hepatocellular carcinoma," Abstract, EASL LiverTree™, 2017.

Zeballos et al., "The role of six transmembrane epithelial antigen of the prostate 2 in hepatocellular carcinoma," *Proceedings: AACR Annual Meeting, Cancer Res.*, 77(Suppl 13):Abstract 5425, 2017.

Zheng et al., "RNA interference reveals tumor-promoting roles of Integrin alpha 6 (ITGA6) in hepatocellular carcinoma," AACR Annual Meeting, Abstract 4642, 2019.

Yang et al., "STEAP2 is down-regulated in breast cancer tissue and suppresses PI3K/AKT signaling and breast cancer cell invasion in vitro and in vivo," *Cancer Biology & Therapy*, 21(3):278-291, 2020.

\* cited by examiner

SEQUENCE LISTING

```
<160> NUMBER OF SEQ ID NOS: 5

<210> SEQ ID NO 1
<211> LENGTH: 58
<212> TYPE: DNA
<213> ORGANISM: Artificial Sequence
<220> FEATURE:
<223> OTHER INFORMATION: Synthetic primer

<400> SEQUENCE: 1
ccgggccagt ggtggtagct ataagctcga gcttatagct accaccactg gcttttttg        58

<210> SEQ ID NO 2
<211> LENGTH: 19
<212> TYPE: DNA
<213> ORGANISM: Artificial Sequence
<220> FEATURE:
<223> OTHER INFORMATION: Synthetic primer

<400> SEQUENCE: 2
caacaauauu caagcgcga                                                    19

<210> SEQ ID NO 3
<211> LENGTH: 19
<212> TYPE: DNA
<213> ORGANISM: Artificial Sequence
<220> FEATURE:
<223> OTHER INFORMATION: Synthetic primer

<400> SEQUENCE: 3
agucuuaauc cuaugcaaa                                                    19

<210> SEQ ID NO 4
<211> LENGTH: 19
<212> TYPE: DNA
<213> ORGANISM: Artificial Sequence
<220> FEATURE:
<223> OTHER INFORMATION: Synthetic primer

<400> SEQUENCE: 4
ggccagauga gcuaaauua                                                    19

<210> SEQ ID NO 5
<211> LENGTH: 19
<212> TYPE: DNA
<213> ORGANISM: Artificial Sequence
<220> FEATURE:
<223> OTHER INFORMATION: Synthetic primer

<400> SEQUENCE: 5
acaaguaugc ugucaaauu                                                    19
```

STEAP2 INHIBITORS FOR THE TREATMENT OF LIVER CANCERS

This application is a national phase application under 35 U.S.C. § 371 of International Application No. PCT/US2018/016212, filed Jan. 31, 2018, which claims the benefit of U.S. Provisional Patent Application No. 62/452,695, filed Jan. 31, 2017, the entirety of each of which is incorporated herein by reference.

BACKGROUND OF THE INVENTION

1. Field of the Invention

The present invention relates generally to the field of molecular biology and medicine. More particularly, it concerns treatments for cancers such as hepatocellular carcinoma.

2. Description of Related Art

Hepatocellular carcinoma (HCC) is a primary malignancy of the liver and presents significant clinical challenges for patients and society. HCC occurs predominantly in patients with underlying chronic liver disease and cirrhosis. Tumors progress with local expansion, intrahepatic spread, and distant metastases.

HCC is now the third leading cause of cancer deaths worldwide, with over 500,000 people affected. The incidence of HCC is highest in Asia and Africa, where the endemic high prevalence of hepatitis B and hepatitis C strongly predisposes to the development of chronic liver disease and subsequent development of HCC.

Although some improvements in diagnosis of HCC has been made, significant challenges and problems remain for the treatment of HCC. The presentation of HCC has evolved significantly over the past few decades. Whereas in the past, HCC generally presented at an advanced stage with right-upper-quadrant pain, weight loss, and signs of decompensated liver disease, some improvements have been made in identifying the disease at a much earlier stage as a consequence of the routine screening of patients with known cirrhosis using cross-sectional imaging studies and serum alpha-fetoprotein (AFP) measurements.

Nonetheless, chemotherapeutics have been generally unsuccessful for the treatment of HCC. The most active single agent drugs tested have been doxorubicin, cisplatin, fluorouracil; however, response rates have typically been observed at about 10%, and the treatment has showed no clear impact on overall survival (Simonetti, 1997).

The threat of HCC is expected to continue to grow in the coming years (Llovet, 2004). The peak incidence of HCC associated with hepatitis C virus (HCV) infection has not yet occurred. There is also a growing problem with cirrhosis, which develops in the setting of nonalcoholic fatty liver disease (NAFLD), or nonalcoholic steatohepatitis (NASH). NASH typically develops in the setting of obesity, type 2 diabetes, dyslipidemia, and hypertension. Liver resection can benefit some patients, although this benefit is usually transient. A few patients may be treated by liver transplantation; however, organ shortages remain and this approach is not a viable option for many or most patients with HCC. Clearly, there exists a need for new and improved methods for treating HCC.

SUMMARY OF THE INVENTION

The present invention overcomes limitations in the prior art by providing new methods for the treatment of liver cancers. The present invention is based, in part, on the discovery that STEAP2 is overexpressed in hepatocellular carcinoma (HCC) and that STEAP2 may contribute to the development of the disease. In some embodiments, an inhibitor of STEAP2 (e.g., a siRNA, an inhibitory nucleic acid, or an antibody) may be used to treat a liver cancer such as HCC.

As shown in the below examples, increased STEAP2 expression was observed in hepatocellular carcinoma (HCC) tumors from human patients, as compared to corresponding adjacent non-tumor liver tissues. Additionally, the increase in STEAP2 mRNA expression in HCC tissues was observed to be more pronounced and even larger in HCC tumors from Hispanic subjects as compared to tissues from Caucasian subjects. RNA deep sequencing data from Hispanic patients and Caucasian patients was also evaluated, and STEAP2 expression data further supported these findings. In some embodiments, it is anticipated that Hispanic patients may particularly benefit from inhibition of STEAP2 to treat a liver cancer such as HCC. Transient knockdown of STEAP2 impaired the growth and migration of two HCC cell lines. Knockdown and overexpression of STEAP2 in the HCC cell lines may be used to measure STEAP2 function in cell growth (e.g., proliferation or survival) and tumorigenicity in immune deficient mice in vivo. Stable knockdown of STEAP2 in multiple HCC cell lines resulted in: decreased proliferation, decreased cell migration, and decreased anchorage independent growth of the HCC cells. In contrast, overexpression of STEAP2 did not affect proliferation of HCC cells, but increased migration and colony formation in the HCC cell lines. The observed data support the use of STEAP2 inhibitors to treat liver cancers such as HCC.

An aspect of the present invention relates to a method of treating a liver cancer in a mammalian subject comprising administering a therapeutically effective amount of a STEAP2 inhibitor to the subject. In some embodiments, the liver cancer is hepatocellular carcinoma (HCC). The hepatocellular carcinoma may be a fibrolamellar carcinoma. In some embodiments, the liver cancer is a primary liver cancer, a secondary liver cancer, an angiosarcoma, a hemangiosarcoma, a hepatoblastoma, a cholangiocarcinoma, a pre-malignant lesions of the liver, or an adenoma. The liver cancer may be non-metastatic or metastatic. The STEAP2 inhibitor may be an antibody or an inhibitory nucleic acid. In some embodiments, the inhibitor is an inhibitory nucleic acid (e.g., a small interfering RNA (siRNA), a double-stranded RNA (dsRNA), a microRNA (miRNA), or a short hairpin RNA (shRNA)). In some embodiments, the STEAP2 inhibitor is a siRNA. In some embodiments, the nucleic acid has been chemically modified to reduce degradation or contains one or more chemically modified nucleic acid analogs. In some embodiments, the nucleic acid is a locked nucleic acid (LNA). The inhibitory nucleic acid may be comprised in liposomes or nanoparticles such as, e.g., neutral liposomes or cationic liposomes. In some embodiments, the liposomes comprise a phosphatidylcholine, a phosphatidylethanolamine phospholipid, DOTAP, cholesterol, or chitosan. In some embodiments, the siRNA comprises or consists of siRNA J-010739-09 (CAACAAUAUU-CAAGCGCGA; SEQ ID NO:2), siRNA J-010739-10 (AGUCUUAAUCCUAUGCAAA; SEQ ID NO:3), siRNA J-010739-11 (GGCCAGAUGAGCUAAAUUA; SEQ ID NO:4), siRNA J-010739-12 (ACAAGUAUGCUGU-CAAAUU; SEQ ID NO:5), or STEAP2 shRNA (CCGGGCCAGTGGTGGTAGCTATAAGCTCGAGCT-TATAGCTACCACCACTGGCTT TTTG; SEQ ID NO:1). The STEAP2 inhibitor may be an antibody, such as a humanized antibody. In some embodiments, the subject is a human (e.g., a Caucasian subject or a Hispanic subject). The STEAP2 inhibitor may be administered parenterally, intravenously, intra-hepatic portal vein, intramuscularly, intraperitoneally, or intra-tumorally. In some embodiments, the method further comprises administering a second anti-cancer therapy to the subject. The second anti-cancer therapy may be, e.g., a surgery, a chemotherapy, an immunotherapy, a liver resection, cryoablation, percutaneous ethanol injection, radiofrequency ablation, transarterial chemoembolization, radiotherapy, radiation therapy, radioembolization, a molecularly targeted therapy, a hormone therapy, a gene therapy, metal ion therapy, or a diet therapy.

Another aspect of the present invention relates to a pharmaceutical composition comprising a STEAP2 inhibitor for use in the treatment of a liver cancer in a mammalian subject. The subject may be a human (e.g., a Caucasian subject or a Hispanic subject). In some embodiments, the STEAP2 inhibitor is an antibody or an inhibitory nucleic acid (e.g., a small interfering RNA (siRNA), double-stranded RNA (dsRNA), microRNAs (miRNA), or a short hairpin RNA (shRNA)). The composition may further comprise a pharmaceutical carrier. In some embodiments, the STEAP2 inhibitor is comprised in liposomes or nanoparticles such as, e.g., neutral liposomes or cationic liposomes. In some embodiments, the liposomes comprise a phosphatidylcholine, a phosphatidylethanolamine phospholipid, DOTAP, cholesterol, or chitosan. In some embodiments, the liver cancer is hepatocellular carcinoma (HCC).

Yet another aspect of the present invention relates to the use of a STEAP2 inhibitor for the manufacture of a medicament for the treatment of a liver cancer. The subject may be a human (e.g., a Caucasian subject or a Hispanic subject). In some embodiments, the STEAP2 inhibitor is an antibody or an inhibitory nucleic acid (e.g., a small interfering RNA (siRNA), double-stranded RNA (dsRNA), microRNAs (miRNA), or a short hairpin RNA (shRNA)). In some embodiments, the STEAP2 inhibitor is comprised in liposomes or nanoparticles. In some embodiments, the liposomes are neutral liposomes or cationic liposomes. The liposomes may comprise a phosphatidylcholine, a phosphatidylethanolamine phospholipid, DOTAP, cholesterol, or chitosan. In some embodiments, the liver cancer is hepatocellular carcinoma (HCC).

Another aspect of the present invention relates to a method of diagnosing a liver cancer in a mammalian subject comprising: a) obtaining a biological sample from the subject; and b) measuring STEAP2 expression in the biological sample, wherein an increase in STEAP2 expression in the sample indicates an increased risk of a liver cancer in the subject. The biological sample may comprise liver tissue, a blood sample, a body fluid comprising STEAP2 mRNA, or a liver biopsy. The subject may be a human (e.g., a Caucasian subject or a Hispanic subject). In some embodiments, the measuring is performed using northern blotting, Western blotting, a polymerase chain reaction (PCR) assay, fluorescent in situ hybridization (FISH), serial analysis of gene expression (SAGE), in situ hybridization, immunohistochemistry, an immunoassay, an expression array, a microarray, a lateral flow assay, enzyme-linked immunosorbent assay (ELISA), quantitative reverse transcriptase PCR (RT-PCR), a radioimmunoassay (RIA), RNase protection assay, RNA sequencing or mass spectrometry. In some embodiments, the subject has a liver cancer (e.g., a metastatic or non-metastatic liver cancer, HCC). In some embodiments, the subject does not have a liver cancer. In some embodiments, the liver cancer is hepatocellular carcinoma (HCC).

The method may further comprises administering an anti-cancer therapy to the subject such as, e.g., a surgery, a chemotherapy, an immunotherapy, a liver resection, cryoablation, percutaneous ethanol injection, radiofrequency ablation, transarterial chemoembolization, radiotherapy, radiation therapy, radioembolization, a molecularly targeted therapy, a hormone therapy, a gene therapy, metal ion therapy or a diet therapy. The method may further comprises administering a STEAP2 inhibitor to the subject. In some embodiments, the STEAP2 inhibitor is a small interfering RNA (siRNA), double-stranded RNA (dsRNA), microRNAs (miRNA), or a short hairpin RNA (shRNA). In some embodiments, the STEAP2 inhibitor is a STEAP2-targeting siRNA. In some embodiments, the subject is Hispanic.

"Nucleic acid" or "oligonucleotide" or "polynucleotide" used herein refers to at least two nucleotides covalently linked together. The depiction of a single strand also defines the sequence of the complementary strand. Thus, a nucleic acid encompasses the complementary strand of a depicted single strand. Variants of a nucleic acid may be used for the same purpose as a given nucleic acid. Nucleic acids may be obtained by chemical synthesis methods or by recombinant methods. A nucleic acid will generally contain phosphodiester bonds, although nucleic acid analogs may be included that may have at least one different linkage, e.g., phosphoramidate, phosphorothioate, phosphorodithioate, or O-methylphosphoroamidite linkages and peptide nucleic acid backbones and linkages. Other analog nucleic acids include those with positive backbones; non-ionic backbones, and non-ribose backbones, including those described in U.S. Pat. Nos. 5,235,033 and 5,034,506, which are incorporated by reference. Nucleic acids containing one or more non-naturally occurring or modified nucleotides are also included within one definition of nucleic acids. The modified nucleotide analog may be located for example at the 5'-end and/or the 3'-end of the nucleic acid molecule. Representative examples of nucleotide analogs may be selected from sugar- or backbone-modified ribonucleotides. It should be noted, however, that also nucleobase-modified ribonucleotides, i.e. ribonucleotides, containing a non-naturally occurring nucleobase instead of a naturally occurring nucleobase such as uridines or cytidines modified at the 5-position, e.g., 5-(2-amino)propyl uridine, 5-bromo uridine; adenosines and guanosines modified at the 8-position, e.g., 8-bromo guanosine; deaza nucleotides, e.g., 7-deaza-adenosine; O- and N-alkylated nucleotides, e.g., N6-methyl adenosine are suitable. The 2'-OH-group may be replaced by a group selected from H, OR, R, halo, SH, SR, $NH_2$, NHR, $NR_2$ or CN, wherein R is $C_1$-$C_6$ alkyl, alkenyl or alkynyl and halo is F, Cl, Br or I. Modified nucleotides also include nucleotides conjugated with cholesterol through, e.g., a hydroxyprolinol linkage as described in Krutzfeldt et al. (2005); Soutschek et al. (2004); and U.S. Patent Publication No. 20050107325, which are incorporated herein by reference. Modified nucleotides and nucleic acids may also include locked nucleic acids (LNA), as described in U.S. Patent Publication No. 2002/0115080, U.S. Pat. Nos. 6,268,490, and 6,770,748, which are incorporated herein by reference. LNA nucleotides include a modified extra methylene "bridge" connecting the 2' oxygen and 4' carbon of the ribose ring. The bridge "locks" the ribose in the 3'-endo (North) conformation, which is often found in the A-form of DNA or RNA. LNA nucleotides can be mixed with DNA or RNA bases in the oligonucleotide whenever desired. Such oligomers are commercially available from companies including Exiqon (Vedbaek, Denmark). Additional modified nucleotides and nucleic acids are described in U.S. Patent Publication Nos.

2005/0182005, which is incorporated herein by reference. Modifications of the ribose-phosphate backbone may be done for a variety of reasons, e.g., to increase the stability and half-life of such molecules in physiological environments, to enhance diffusion across cell membranes, or as probes on a biochip. Mixtures of naturally occurring nucleic acids and analogs may be made; alternatively, mixtures of different nucleic acid analogs.

As used herein, "increased expression" refers to an elevated or increased level of expression in a cancer sample relative to a suitable control (e.g., a non-cancerous tissue or cell sample, or a reference standard), wherein the elevation or increase in the level of gene expression is statistically-significant ($p<0.05$). Whether an increase in the expression of a gene in a cancer sample relative to a control is statistically significant can be determined using an appropriate t-test (e.g., one-sample t-test, two-sample t-test, Welch's t-test) or other statistical test known to those of skill in the art. Genes that are overexpressed in a cancer can be, for example, genes that are known, or have been previously determined, to be overexpressed in a cancer.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
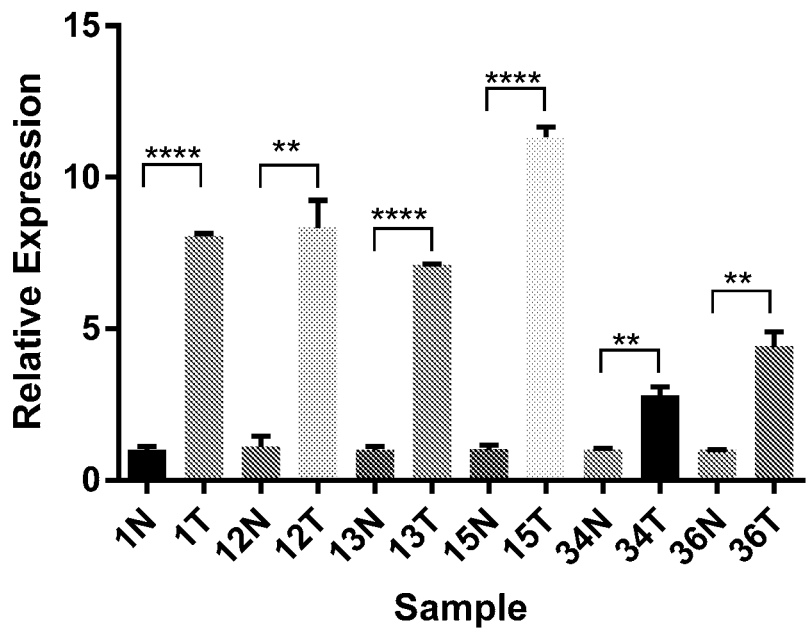
FIG. 1: STEAP2 mRNA expression. Comparison of STEAP2 mRNA levels between adjacent non-tumor (N) and hepatocellular carcinoma (HCC) tumor (T) from six Hispanic and six Caucasian patients. mRNA levels were measured by real time RT-PCR. Tumor STEAP2 mRNA level was normalized by its own adjacent non-tumor tissue STEAP2 mRNA level and is expressed as Relative Expression. *$P<0.01$. $P<0.01$, *$P<0.001$, ****$P<0.0001$
Figure 1:
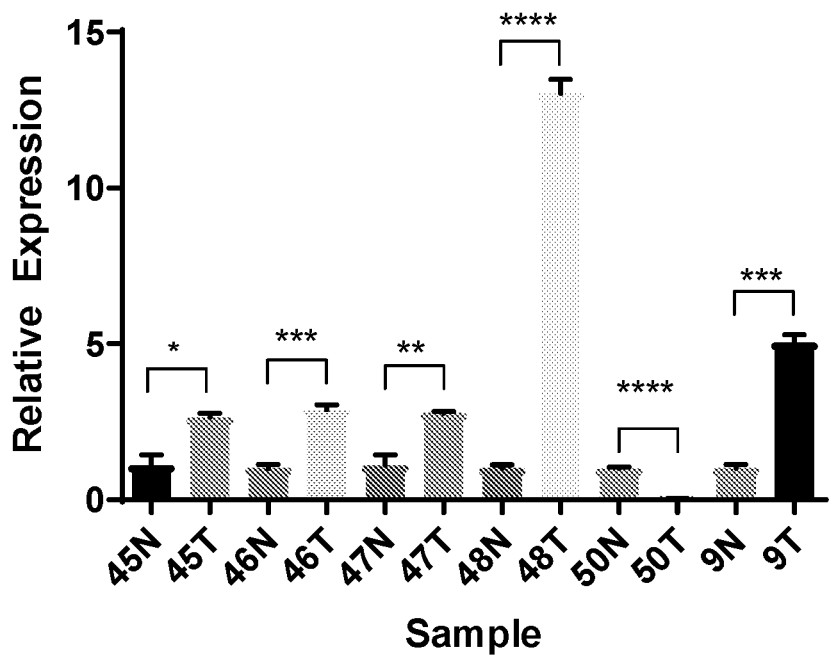

The present invention provides, in some aspects, treatments for liver cancers such as, e.g., HCC. In some aspects, a STEAP2 inhibitor (e.g., a STEAP2 inhibitory nucleic acid such as a siRNA) is administered to a mammalian subject, such as a human to treat a HCC. It is anticipated that the methods provided herein may be used to treat a variety of liver cancers such as, e.g., a primary liver cancer, a secondary liver cancer, an angiosarcoma, a hepatoblastoma, cholangiocarcinoma, or pre-malignant lesions of the liver such as adenomas. Detection of STEAP2 (e.g., in a liver tissue sample) may be used, in some aspects, to predict risk for a liver cancer such as HCC.

I. STEAP2 Inhibitors

STEAP2 (also called STEAP2 metalloreductase; human Gene ID: 261729) is a member of the six-6-transmembrane epithelial antigen of prostate (STEAP) family. STEAP proteins expressed in mammals have activity as metalloreductases, and play a role in metal metabolism. STEAP proteins can also play a role in various biologic processes, including molecular trafficking in endocytic and exocytic pathways, cell proliferation, and apoptosis. Because of its metalloreductase activity, STEAP2 contributes to proper erythrocyte $Fe^{3+}$ and $Cu^{2+}$ uptake and reduction to $Fe^{2+}$ and $Cu^+$ STEAP2 can also function in the movement of proteins in either direction between the Golgi complex and the plasma membrane in endocytic and exocytic pathways, supporting the idea that STEAP2 may function in regulation of protein delivery and sorting mechanisms for proteins (Korkmaz, 2002). STEAP2 is highly expressed in epithelial cells of the prostate, particularly in the plasma membrane and Golgi complex, in association with the trans-Golgi network (TGN) and early endosomes. Besides the prostate, its expression is also detectable in other normal human tissues, for example, heart, brain, pancreas, ovary, skeletal muscle, mammary gland, testis, uterus, kidney, lung, trachea, and liver (Korkmaz, 2002; Porkka, 2002).

In some aspects, an inhibitor of STEAP2 is administered to a subject (e.g., a human patient) to treat a liver cancer such as, e.g., HCC. In certain aspects this can be accomplished by administration of an inhibitory nucleic acid that reduces expression of STEAP2. Examples of inhibitory nucleic acids include, without limitation, antisense nucleic acids, small interfering RNAs (siRNAs), double-stranded RNAs (dsRNAs), microRNAs (miRNA) and short hairpin RNAs (shRNA) that are complimentary to all or part of STEAP2 mRNA. An inhibitory nucleic acid can, for example, inhibit the transcription of a gene in a cell, mediate degradation of an mRNA in a cell and/or inhibit the translation of a polypeptide from a mRNA. Typically an inhibitory nucleic acid may be from 16 to 1000 or more nucleotides long, and in certain embodiments from 18 to 100 nucleotides long. In certain embodiments, the inhibitory nucleic acid may be 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides long. In some aspects an inhibitory nucleic acid may comprise one or more modified nucleotide or nucleic acid analog. Typically, an inhibitory nucleic acid will inhibit the expression of a single gene within a cell; however, in certain embodiments, the inhibitory nucleic acid will inhibit the expression of more than one gene within a cell.

Inhibitory nucleic acids are well known in the art. For example, siRNA, shRNA and double-stranded RNA have been described in U.S. Pat. Nos. 6,506,559 and 6,573,099, as well as in U.S. Patent Publications 2003/0051263, 2003/0055020, 2004/0265839, 2002/0168707, 2003/0159161, and 2004/0064842, all of which are herein incorporated by reference in their entirety.

In some aspects, an inhibitory nucleic acid can form a double-stranded structure. For example, the double-stranded structure may result from two separate nucleic acid molecules that are partially or completely complementary. In certain embodiments, the inhibitory nucleic acid may comprise only a single nucleic acid or nucleic acid analog and form a double-stranded structure by complementing with itself (e.g., forming a hairpin loop). The double-stranded structure of the inhibitory nucleic acid may comprise 16 to 500 or more contiguous nucleobases. For example, the inhibitory nucleic acid may comprise 17 to 35 contiguous nucleobases, more preferably 18 to 30 contiguous nucleobases, more preferably 19 to 25 nucleobases, more preferably 20 to 23 contiguous nucleobases, or 20 to 22 contiguous nucleobases, or 21 contiguous nucleobases that are complementary to a STEAP2 mRNA. In some embodiments, the siRNA is from 25-35 nucleotides or from 19-25 nucleotides in length. Methods for using such siRNA or double-stranded RNA molecules have been described in U.S. Pat. Nos. 6,506,559 and 6,573,099, as well as in U.S. Applications 2003/0051263, 2003/0055020, 2004/0265839, 2002/0168707, 2003/0159161, 2004/0064842, each of which are herein incorporated by reference in their entirety.

In some embodiments, inhibitory nucleic acid molecules contemplated for use according to the embodiments include but are not limited to molecules that comprise 15, 16, 17, 18, 19, 20, 21, 22, 23, 24, 25, 26, 27, 28, 29, 30, 35, 40, 45, 50, 55, 60, 65, 70, 75, 80, 85, 90, 95, 100 or more nucleotides that are complementary to the nucleotide sequence encoding a human STEAP2 mRNA (e.g., Refseq Nos.: NM 001040665.1, NM 001040666.1, NM_001244944.1, NM_001244945.1, or NM_001244946.1; predicted transcripts based on GRCh38.p7 Primary Assembly for humans: XM_017011956.1, XM_006715921.3, XM_017011953.1, XM_017011954.1, XM_017011955.1, XM_017011957.1, XM_017011958.1).

To improve the effectiveness of siRNA-mediated gene silencing, guidelines for selection of target sites on mRNA have been developed for optimal design of siRNA (Soutschek et al., 2004; Wadhwa et al., 2004). These strategies may allow for rational approaches for selecting siRNA sequences to achieve maximal gene knockdown. To facilitate the entry of siRNA into cells and tissues, a variety of vectors including plasmids and viral vectors such as adenovirus, lentivirus, and retrovirus have been used (Wadhwa et al., 2004).

Within an inhibitory nucleic acid, the components of a nucleic acid need not be of the same type or homogenous throughout (e.g., an inhibitory nucleic acid may comprise a nucleotide and a nucleic acid or nucleotide analog). Typically, an inhibitory nucleic acid form a double-stranded structure; the double-stranded structure may result from two separate nucleic acids that are partially or completely complementary. In certain embodiments of the present invention, the inhibitory nucleic acid may comprise only a single nucleic acid (polynucleotide) or nucleic acid analog and form a double-stranded structure by complementing with itself (e.g., forming a hairpin loop). The double-stranded structure of the inhibitory nucleic acid may comprise 16-500 or more contiguous nucleobases, including any range therein. The inhibitory nucleic acid may comprise 17 to 35 contiguous nucleobases, more particularly 18 to 30 contiguous nucleobases, more particularly 19 to 25 nucleobases, more particularly 20 to 23 contiguous nucleobases, or 20 to 22 contiguous nucleobases, or 21 contiguous nucleobases that hybridize with a complementary nucleic acid (which may be another part of the same nucleic acid or a separate complementary nucleic acid) to form a double-stranded structure. In some embodiments, the inhibitory nucleic acid is 17, 18, 19, 20, 21, 22, 23, 24, 25, 26, 27, 28, 29, 30, 31, 32, 33, 34, 35 nucleic acids in length, or any range therein. In some embodiments, the inhibitory nucleic acid is a siRNA wherein the siRNA is 20, 21, 22, 23, 24, or 25 nucleotides in length.

siRNA can be obtained from commercial sources, natural sources, or can be synthesized using any of a number of techniques well-known to those of ordinary skill in the art. For example, commercial sources of predesigned siRNA include Invitrogen's Stealth™ Select technology (Carlsbad, Calif.), Ambion® (Austin, Tex.), and Qiagen® (Valencia, Calif.). An inhibitory nucleic acid that can be applied in the compositions and methods of the present invention may be any nucleic acid sequence that has been found by any source to be a validated downregulator of a STEAP2.

In some embodiments, the invention features an isolated siRNA molecule of at least 19, preferably 20-30, more preferably 20-25 nucleotides having at least one strand that is substantially complementary to at least ten but no more than thirty consecutive nucleotides of a nucleic acid that encodes STEAP2, and that reduces the expression of STEAP2. In some embodiments of the present invention, the siRNA molecule has at least one strand that is substantially complementary to at least ten but no more than thirty consecutive nucleotides of the mRNA that encodes STEAP2.

In some embodiments, the siRNA molecule is at least 75, 80, 85, or 90% homologous, particularly at least 95%, 99%, or 100% similar or identical, or any percentages in between the foregoing (e.g., the invention contemplates 75% and greater, 80% and greater, 85% and greater, and so on, and said ranges are intended to include all whole numbers in between), to at least 10, preferably at least 16, 17, 18, 19, 20, or 21 contiguous nucleotides of any of the nucleic acid sequences encoding a full-length STEAP2 protein.

The siRNA may also comprise an alteration of one or more nucleotides. Such alterations can include the addition of non-nucleotide material, such as to the end(s) of the 19 to 25 nucleotide RNA or internally (at one or more nucleotides of the RNA). In some embodiments, the RNA molecule contains a 3'-hydroxyl group. Nucleotides in the RNA molecules of the present invention can also comprise non-standard nucleotides, including non-naturally occurring nucleotides or deoxyribonucleotides. The double-stranded oligonucleotide may contain a modified backbone, for example, phosphorothioate, phosphorodithioate, or other modified backbones known in the art, or may contain non-natural internucleoside linkages. Additional modifications of siRNAs (e.g., 2'-O-methyl ribonucleotides, 2'-deoxy-2'-fluoro ribonucleotides, "universal base" nucleotides, 5-C-methyl nucleotides, one or more phosphorothioate internucleotide linkages, and inverted deoxyabasic residue incorporation) can be found in U.S. Publication 2004/0019001 and U.S. Pat. No. 6,673,611 (each of which is incorporated by reference in its entirety). Collectively, all such altered nucleic acids or RNAs described above are referred to as modified siRNAs.

In some embodiments, the inhibitory nucleic acid is capable of decreasing the expression of STEAP2 (e.g., STEAP25) by at least 10%, at least 20%, at least 30%, or at least 40%, at least 50%, at least 60%, or at least 70%, at least 75%, at least 80%, at least 90%, at least 95% or more or any ranges in between the foregoing. In some embodiments, the expression of STEAP2 is decreased via the RNAi pathway.

Certain embodiments of the present invention pertain to methods of inhibiting expression of a gene encoding STEAP2 in a cell by introduction of inhibitory nucleic acids into the cell. Introduction of siRNA into cells can be achieved by methods known in the art, including for example, microinjection, electroporation, or transfection of a vector comprising a nucleic acid from which the siRNA can be transcribed. Alternatively, a siRNA can be directly introduced into a cell in a form that is capable of binding to target STEAP2 mRNA transcripts. To increase durability and membrane-permeability the siRNA may be combined or modified with liposomes, poly-L-lysine, lipids, cholesterol, lipofectine or derivatives thereof. In certain aspects cholesterol-conjugated siRNA can be used (see, Song et al., 2003).

Methods for preparing and using inhibitory nucleic acid molecules in accordance with the embodiments are well known in the art. Likewise methods for delivering inhibitory nucleic acid molecule molecules into cells are also well known in the art. For example inhibitory nucleic acid (or inhibitory nucleic acid expression vectors) may be delivered in nanoparticles or liposomes such as 1,2-bis(oleoyloxy)-3-(trimethyl ammonio)propane (DOTAP) and cholesterol liposomes or cationic liposomes, e.g., as described in U.S. Pat. No. 6,806,084. Additionally, in some embodiments the inhibitory nucleic acid may be delivered using an expression vector system for delivery, e.g., using a viral vector. Some non-limiting examples of viruses contemplated herein for nucleic acid delivery include herpesviral vectors; adenoviral vectors, retroviral and lentiviral vectors (e.g., as described in U.S. patent App. 20050014166), and adeno-associated viral vectors (e.g., as described in U.S. Pat. No. 5,139,941 or 4,797,368). In some embodiments, the STEAP2 inhibitory nucleic acid (e.g., siRNA) may be administered via a neutral or non-charged liposome, e.g., using liposomes as described in U.S. Pat. No. 8,895,717. In some embodiments, the STEAP2 inhibitory nucleic acid (e.g., siRNA) may be administered via a neutral or non-charged liposome, e.g., using liposomes as described in U.S. Pat. No. 8,734,853. For example, in some embodiments, the liposome comprises one or more neutral phospholipids such as a phosphatidylcholine or a phosphatidylethanolamine phospholipid. A variety of compounds may be included in the liposomes such as, e.g., egg phosphatidylcholine ("EPC"), dilauryloylphosphatidylcholine ("DLPC"), dimyristoylphosphatidylcholine ("DMPC"), dipalmitoylphosphatidylcholine ("DPPC"), distearoylphosphatidylcholine ("DSPC"), 1-myristoyl-2-palmitoyl phosphatidylcholine ("MPPC"), 1-palmitoyl-2-myristoyl phosphatidylcholine ("PMPC"), 1-palmitoyl-2-stearoyl phosphatidylcholine ("PSPC"), 1-stearoyl-2-palmitoyl phosphatidylcholine ("SPPC"), dimyristyl phosphatidylcholine ("DMPC"), 1,2-distearoyl-sn-glycero-3-phosphocholine ("DAPC"), 1,2-diarachidoyl-sn-glycero-3-phosphocholine ("DBPC"), 1,2-dieicosenoyl-sn-glycero-3-phosphocholine ("DEPC"), palmitoyloeoyl phosphatidylcholine ("POPC"), dilinoleoylphosphatidylcholine disteroylphophatidylethanolamine ("DSPE"), dimyristoyl phosphatidylethanolamine ("DMPE"), dipalmitoyl phosphatidylethanolamine ("DPPE"), palmitoyloeoyl phosphatidylethanolamine ("POPE"), dioleoylphosphatidylethanolamine ("DOPE") or dioleoylphosphatidylcholine ("DOPC"). The STEAP2 inhibitor or STEAP2 inhibitory nucleic acid may be administered parenterally, intravenously, intra-hepatic portal vein, intramuscularly, intraperitoneally, or intra-tumorally.

In certain aspects, the inhibitory nucleic acid may also be expressed in cells from an expression vector. For example, expression can be under the transcriptional control of a RNA Polymerase III promoter, such as the U6 promoter. Such promoters may be particularly useful for the expression of short RNA sequences, such as siRNA molecules. In certain aspects tissue specific promoters may also be employed, for example promoter that express nucleic acids in the liver. Specific vectors to express inhibitory nucleic acids are well known in the art. For example the commercially available pSUPER RNAi System™ available from OilgoEngine® and the pSilencer™ siRNA expression vectors available from Life Technologies™.

In still a further embodiment, the inhibitor of STEAP2 is a molecule that binds to and inhibits STEAP2 such as, e.g., a small molecule, an aptamer, or an antibody (or fragment thereof) that binds to STEAP2. In some aspects, an aptamer or antibody of the embodiments specifically binds to a human STEAP2. Methods for making and using antibodies are well known in the art and are detailed for example in U.S. Pat. No. 4,816,567, incorporated herein by reference. Likewise, methods for making aptamers, such as by SELEX, are well known and described, e.g., in U.S. Pat. Nos. 6,569,620 and 6,716,580, incorporated herein by reference.

Various antibodies that can selectively bind STEAP2 are known in the art and may be used to treat a liver cancer in a subject in some embodiments. In some embodiments, the antibody is humanized.

II. Combination Therapies

In certain embodiments, a STEAP2 inhibitor is administered to a subject, such as a human subject, in combination with at least one additional therapy. The additional therapy may be radiation therapy, surgery (e.g., hepatectomy and liver transplantation), chemotherapy, microwave ablation, alcohol ablation, chemoembolization, gene therapy, DNA therapy, viral therapy, RNA therapy, immunotherapy, bone marrow transplantation, nanotherapy, monoclonal antibody therapy, or a combination of the foregoing.

In some embodiments, the additional therapy is the administration of small molecule enzymatic inhibitor or anti-metastatic agent. In some embodiments, the additional therapy is the administration of side-effect limiting agents (e.g., agents intended to lessen the occurrence and/or severity of side effects of treatment, such as anti-nausea agents, etc.). In some embodiments, the additional therapy is radiation therapy, a surgery, or a combination of radiation therapy (e.g., gamma irradiation) and surgery. In some embodiments, the additional therapy is therapy with an antiangiogenesis agent (e.g., bevacizumab, or bevacizumab with gemcitabine and oxaliplatin), a tyrosine kinase inhibitor (e.g., sorafenib, erlotinib), a surgery (e.g., a partial hepatectomy), a locally ablative therapy (e.g., intratumoral injection of ethanol or acetic acid, radiofrequency ablation, microwave ablation, laser ablation, nanoknife or cryoablation with liquid nitrogen), a local chemotherapy (e.g., chemoembolism), modulation of local metal ions (e.g., iron, copper), gene therapy, or diet therapy.

A STEAP2 inhibitor therapy may be administered before, during, after, or in various combinations relative to an additional cancer therapy. The administrations may be in intervals ranging from concurrently to minutes to days to weeks. In embodiments where the STEAP2 inhibitor therapy is provided to a patient separately from an additional therapeutic agent, one would generally ensure that a significant period of time did not expire between the time of each delivery, such that the two compounds would still be able to exert an advantageously combined effect on the patient. In such instances, it is contemplated that one may provide a patient with the antibody therapy and the anti-cancer therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

Various combinations may be employed. For the example below an STEAP2 inhibitor is "A" and an anti-cancer therapy is "B":

| A/B/A | B/A/B | B/B/A | A/A/B | A/B/B | B/A/A | A/B/B/B | B/A/B/B |
| B/B/B/A | B/B/A/B | A/A/B/B | A/B/A/B | A/B/B/A | B/B/A/A |
| B/A/B/A | B/A/A/B | A/A/A/B | B/A/A/A | A/B/A/A | A/A/B/A |

Administration of any compound or therapy of the present embodiments to a patient will follow general protocols for the administration of such compounds, taking into account the toxicity, if any, of the agents. Therefore, in some embodiments there is a step of monitoring toxicity that is attributable to combination therapy.

III. Detection of STEAP2 Expression

In some aspects, STEAP2 expression may be evaluated to determine if a subject (e.g., a human patient) has or has an increased risk of having a liver cancer such as, e.g., HCC. As described herein and in the examples below, increased expression of STEAP2 has been observed in HCC tissues and may be involved in or promote the development of liver cancers such as HCC.

Methods for analyzing gene expression or expression of STEAP2 include, but are not limited to, methods based on hybridization analysis of polynucleotides (e.g., mRNA), and analysis of protein expression such as, e.g., proteomics-based methods. Commonly used methods for the quantification of mRNA expression in a sample include northern blotting and in situ hybridization (Parker and Barnes, 1999), RNAse protection assays, and PCR-based methods, such as reverse transcription polymerase chain reaction (RT-PCR) (Weis et al., 1992). In some embodiments, antibodies may be employed to detect STEAP2 protein (e.g., in a liver tissue, liver tissue biopsy, or blood, hepatic fluid) using a variety of techniques which are known to one of skill including, e.g., Western blotting, an immunoassay, immunohistochemistry, etc. Representative methods for sequencing-based gene expression analysis that may be used include Serial Analysis of Gene Expression (SAGE), and gene expression analysis by massively parallel signature sequencing (MPSS).

1. PCR-Based Methods

STEAP2 expression can be analyzed using techniques that employ polymerase chain reaction (PCR). In some embodiments, RT-PCR can be used to compare mRNA levels in different samples (e.g., a biological tissue comprising liver tissue) to examine gene expression signatures. In some embodiments, it is anticipated that STEAP2 expression in a biological sample that contains no or essentially no liver tissue (e.g., a blood sample) may be used to predict risk for a liver cancer such as HCC.

RT-PCR may be performed via techniques well known in art. For example, RT-PCR can be performed using commercially available equipment, such as an ABI PRISM 7700 Sequence Detection System™ (Perkin-Elmer-Applied Biosystems, Foster City, Calif., USA), or Lightcycler® (Roche Molecular Biochemicals, Mannheim, Germany).

A variation of the RT-PCR technique is real time quantitative PCR, which measures PCR product accumulation through a dual-labeled fluorigenic probe, such as a TaqMan™ probe. Real time PCR is compatible both with quantitative competitive PCR, where internal competitor for each target sequence is used for normalization, and with quantitative comparative PCR using a normalization gene contained within the sample, or a housekeeping gene for RT-PCR.

Gene expression may be examined using fixed, paraffin-embedded tissues as the RNA source or fresh tissue such as tissue obtained from a biopsy of hepatic tissue. Examples of methods of examining expression in fixed, paraffin-embedded tissues, are described, for example, in Godfrey et al., 2000; and Specht et. al., 2001.

Another approach for gene expression analysis employs competitive PCR design and automated, high-throughput matrix-assisted laser desorption ionization time-of-flight (MALDI-TOF) MS detection and quantification of oligonucleotides. This method is described by Ding and Cantor, 2003. In some embodiments, the MassARRAY-based gene expression profiling method, developed by Sequenom, Inc. (San Diego, Calif.) can be used.

Additional PCR-based techniques for gene expression analysis include, e.g., differential display (Liang and Pardee, 1992); amplified fragment length polymorphism (iAFLP) (Kawamoto et al., 1999); BeadArray™ technology (Illumina, San Diego, Calif.; Oliphant et al., 2002; Ferguson et al., 2000); BeadsArray for Detection of Gene Expression (BADGE), using the commercially available Luminex100 LabMAP system and multiple color-coded microspheres (Luminex Corp., Austin, Tex.) in a rapid assay for gene expression (Yang et al., 2001); and high coverage expression profiling (HiCEP) analysis (Fukumura et al., 2003).

2. Microarrays

Other techniques for examining gene or protein expression in a sample involve use of microarrays (e.g., a nucleotide microarray, a protein microarray). Microarrays permit simultaneous analysis of a large number of gene expression or protein products. Typically, polynucleotides of interest are plated, or arrayed, on a microchip substrate. The arrayed sequences are then hybridized with nucleic acids (e.g., DNA or RNA) from cells or tissues of interest. The source of mRNA typically is total RNA. If the source of mRNA is liver tissue, mRNA can be extracted.

Microarray approaches are well known in the art. For example, cDNA may be reverse transcribed from mRNA and the cDNA may be quantified using a DNA microarray. Probe-target hybridization of nucleic acids is typically detected and quantified by binding of complementary nucleic acids labelled with a fluorophore, silver, or a chemiluminescent compound, to determine the relative abundance of nucleic acid sequences.

3. Serial Analysis of Gene Expression (SAGE)

STEAP2 expression in samples may also be determined by serial analysis of gene expression (SAGE), which is a method that allows the simultaneous and quantitative analysis of a large number of gene transcripts, without the need of providing an individual hybridization probe for each transcript (see Velculescu et al., 1995; and Velculescu et al., 1997). Briefly, a short sequence tag (about 10-14 nucleotides) is generated that contains sufficient information to uniquely identify a transcript, provided that the tag is obtained from a unique position within each transcript. Then, many transcripts are linked together to form long serial molecules, that can be sequenced, revealing the identity of the multiple tags simultaneously. The expression pattern of a population of transcripts can be quantitatively evaluated by determining the abundance of individual tags, and identifying the gene corresponding to each tag.

4. Protein Detection Methodologies

Immunohistochemical methods are also suitable for detecting the expression of STEAP2. A variety of immunohistochemical methods are well known in the art and may be used with the present invention including, e.g., immunohistochemistry, Western blotting, and fluorescent in situ immunohistochemistry (FISH). Antibodies, such as monoclonal antibodies, specific for STEAP2 may be used to detect expression. The antibodies can be detected by direct labeling of the antibodies themselves, for example, with radioactive labels, fluorescent labels, hapten labels such as, biotin, or an enzyme such as horse radish peroxidase or alkaline phosphatase. Alternatively, unlabeled primary antibody can be used in conjunction with a labeled secondary antibody, comprising antisera, polyclonal antisera or a monoclonal antibody specific for the primary antibody. Immunohistochemistry protocols and kits are well known in the art and are commercially available. A variety of methods for the quantification of proteins are known in the art including, e.g., ELISA, Western blotting, immunohistochemistry, and may be used with the present invention.

Proteomic methods can allow examination of global changes in protein expression in a sample. Proteomic analysis may involve separation of individual proteins in a sample by 2-D gel electrophoresis (2-D PAGE), and identification of individual proteins recovered from the gel, such as by mass spectrometry or N-terminal sequencing, and analysis of the data using bioinformatics. Proteomics methods can be used alone or in combination with other methods for evaluating gene expression.

IV. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Function of Six Transmembrane Epithelial Antigen of Prostate 2 (STEAP2) in Hepatocellular Carcinoma (HCC)

Methods

Tissues:

Paired adjacent non-tumor and HCC tumor tissue were collected from Hispanic and non-Hispanic white patients by the Transplant Center at our university. A small piece of tissue was formalin-fixed, paraffin-imbedded for histology examination by a pathologist to confirm that the adjacent non-tumor tissues did not contain tumor cells and the tumor tissues contained over 75% of tumor cells. The rest of the tissues were cut into small pieces, flash frozen in liquid nitrogen and stored in a liquid nitrogen tank.

RNA Extraction and Sequencing:

Total RNA was extracted from each piece of tissues with RNeasy Mini Kit from Quiagen. RNA samples were deep-sequenced by our university Genomic Sequencing Core Facility. To confirm the data from RNA-sequencing, STEAP2 RNA levels in Hispanic paired samples versus Caucasian paired samples were evaluated by real time RT-PCR.

Gene Knockdown:

A pool of STEAP2 siRNAs (Dharmacon) at 25 nM were transfected into HCC cell lines, such as HUH7 and SNU398, with Dharmafect 4 transfection reagent. The knockdown of STEAP2 was confirmed with real time RT-PCR. The following siRNA sequences from Dharmacon ON-TARGETplus SMARTpool were used: siRNA J-010739-09 (CAACAAUAUUCAAGCGCGA; SEQ ID NO:2), J-010739-10 (AGUCUUAAUCCUAUGCAAA; SEQ ID NO:3), J-010739-11 (GGCCAGAUGAGCUAAAUUA; SEQ ID NO:4), J-010739-12 (ACAAGUAUGCUGU-CAAAUU; SEQ ID NO:5).

MTT Assay:

HUH7 and SNU398 cells ($4 \times 10^3$/well) were seeded into 96-well plates. A pool of STEAP2 siRNAs at 25 nM were transfected into HCC cell lines with Dharmafect 4 transfection reagent. Cell viability was measured 6, 24, 48, 72, 96, 120 and 144 hours post-transfection. An MTT solution (2 mg/mL) was added to each well for 4 hours. The resulting formazan crystals were dissolved in DMSO, and the optical density was measured at 595 nm.

Migration Assay:

48 hours before cell migration assay, a pool for STEAP2 siRNAs (Dharmacon) at 25 nM were transfected into HCC cell lines, such as HUH7 and SNU398, with Dharmafect4 transfection reagent in a 60-mm dish. Cell migration assays were performed in 24-well transwell chambers (Corning Inc., Corning, N.Y., USA) using inserts with an 8-µm pore membrane. Cells (25,000 for SNU398 and 30,000 for HUH7) in serum-free RPMI1640 were seeded in the upper chamber of the insert and RPMI1640 containing 10% fetal bovine serum was added to the lower chamber and followed by incubation for 16 hours. Cells that did not migrate were removed using a cotton tipped swab and ddH20. The migrated cells were fixed and stained using Fisher Health-Care™ Protocol™ Hema3™ fixative and Solutions. Cells were counted under a microscope.

Results

Results from the paired HCC Hispanic RNA sequencing data compared to the paired HCC RNA sequencing data from The Cancer Genome Atlas (TCGA) (mostly Caucasians in this data set) demonstrated that STEAP2 was significantly over-expressed in Hispanics compared to non-Hispanic sequencing data. Real time RT-PCR data validated that the overexpression of STEAP2 in Hispanic HCC tumor tissue compared to adjacent tissue. Knockdown of STEAP2 in the SNU398 HCC cells decreased both proliferation and migration, while in HUH7 cells STEAP2 knockdown decreased migration with very moderate inhibition of proliferation.

As shown in FIG. 1, STEAP2 mRNA levels were measured in non-tumor (N) and hepatocellular carcinoma (HCC) tumor (T) tissues from six Hispanic and six Caucasian patients using real time RT-PCR. Increased expression of STEAP2 was observed in the HCC tumor tissue as compared to non-tumor tissues in both Hispanic and Caucasian subjects. The increase in STEAP2 was even greater in the Hispanic patients, as compared to the Caucasian patients.

Figure 2:
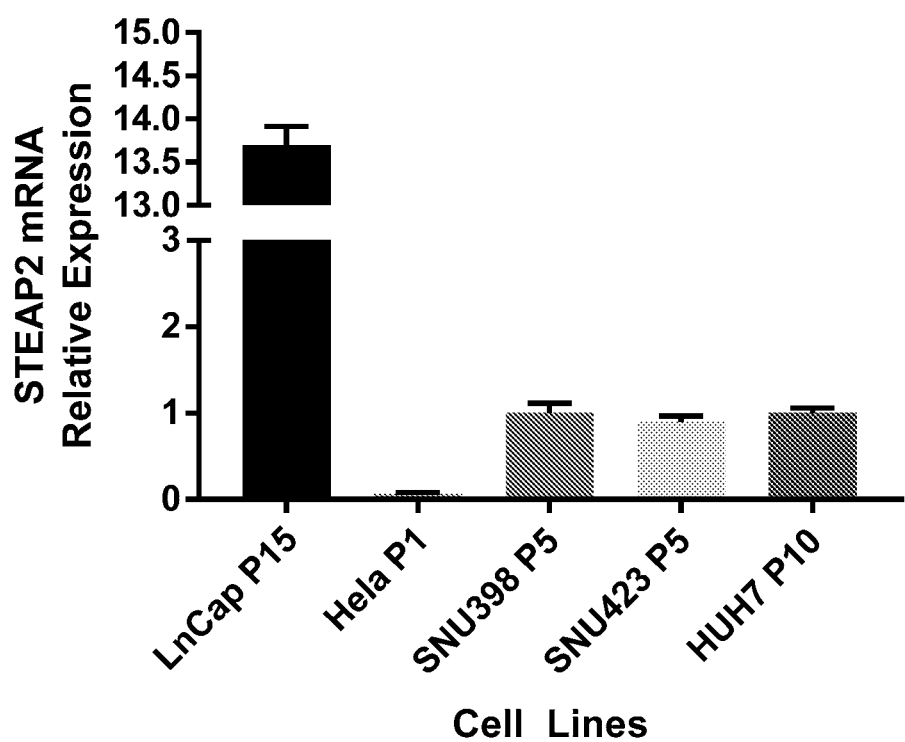
FIG. 2: STEAP2 mRNA levels in human cancer cell lines. STEAP2 mRNA levels were measured using real tine RT-PCR in human prostate cancer LnCap, cervical cancer Hela, and HCC SNU398, SNU423, and HUH7.

As shown in FIG. 2, STEAP2 mRNA levels were measurable with real tine RT-PCR a variety of cancer cell lines, i.e., in human prostate cancer LnCap, cervical cancer Hela, and HCC SNU398, SNU423, and HUH7 cell lines.

Figure 3:
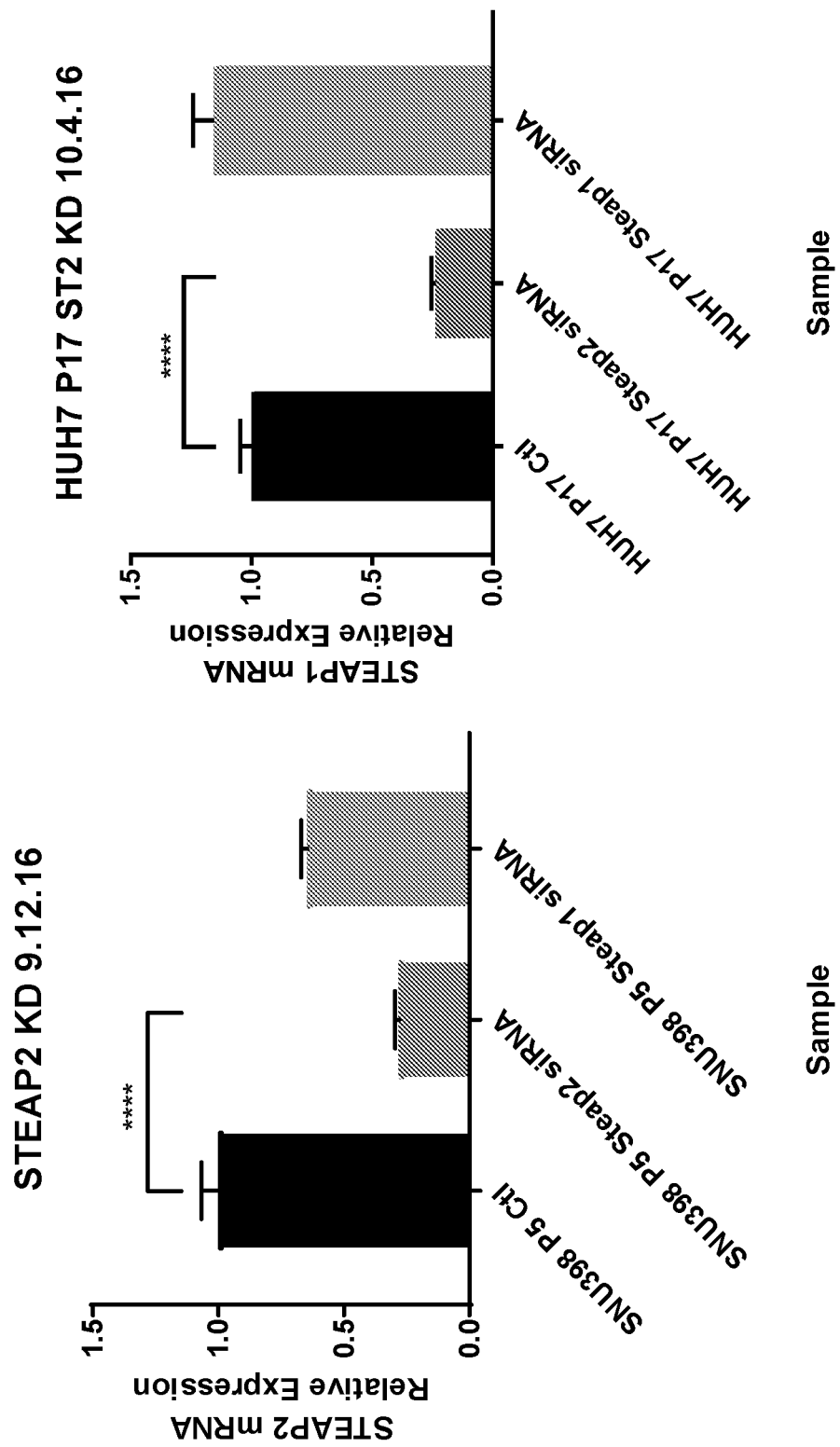
FIG. 3: STEAP2 knockdown with siRNA pool. STEAP2 pool siRNA (25 nM) was used to knockdown STEAP2 in SNU398 and HUH7. mRNA level was measured and demonstrated the specificity of STEAP2 siRNA. Cells were harvested 48 hours after transfection, RNA was isolated, and mRNA levels were measured with real tine RT-PCR. ****$P<0.0001$
Figure 4:
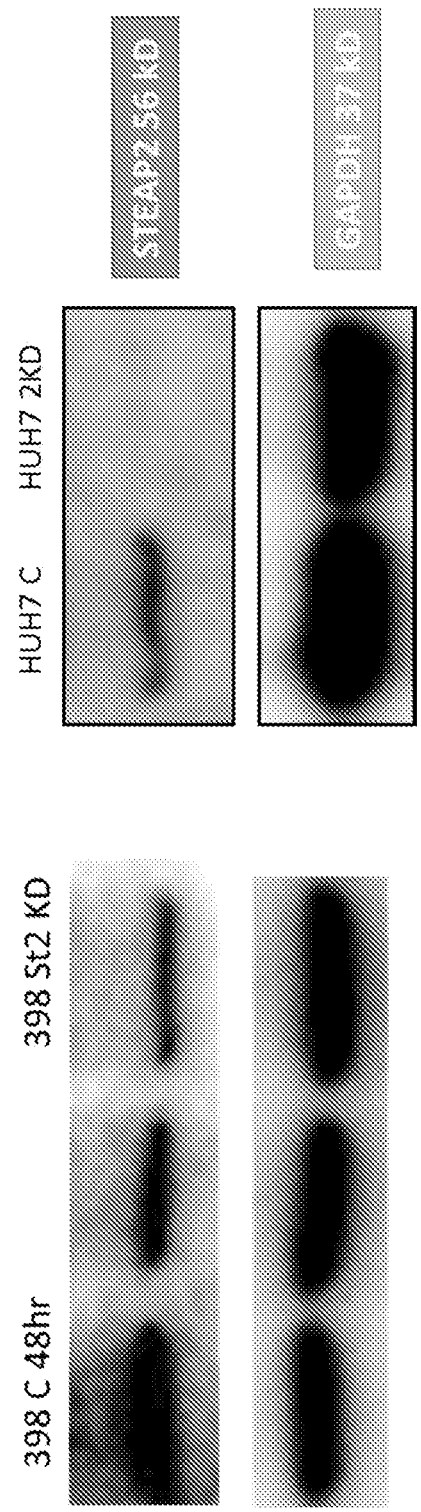
FIG. 4: STEAP2 knockdown in SNU398 and HUH7 HCC cell lines shown using Western Blot. STEAP2 pool siRNA (25 nM) was used to knockdown STEAP2 in SNU398 and HUH7. Cells were harvested 48 hours after transfection, protein was isolated, and protein levels were measured with STEAP2 Antibody (Abcam Ab 174978) via western blot.

STEAP2 siRNA was used to knockdown STEAP2 in HCC cell lines SNU398, SNU423, and HUH7. The knockdown of STEAP2 using the siRNA was observed to be specific based on mRNA and protein expression levels, as shown in FIG. 3 and FIG. 4.

Figure 5:
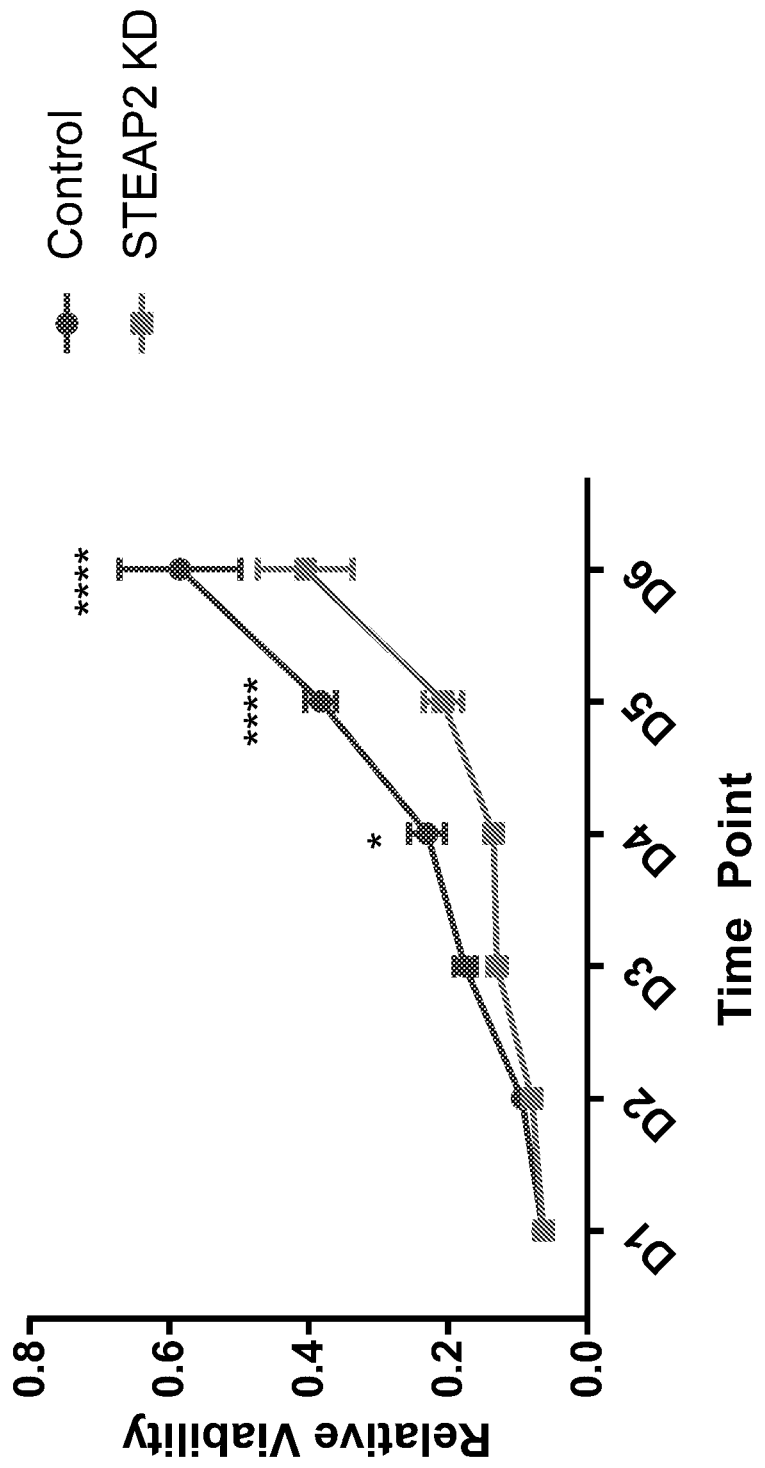
FIG. 5: Knockdown of STEAP2 reduced SNU398 cell viability measured with MTT assay. STEAP2 pool siRNA (25 nM) was used to knockdown STEAP2 in SNU398. Cell viability assay (MTT) was carried out for 6 days. *$P<0.01$, **$P<0.0001$
Figure 6:
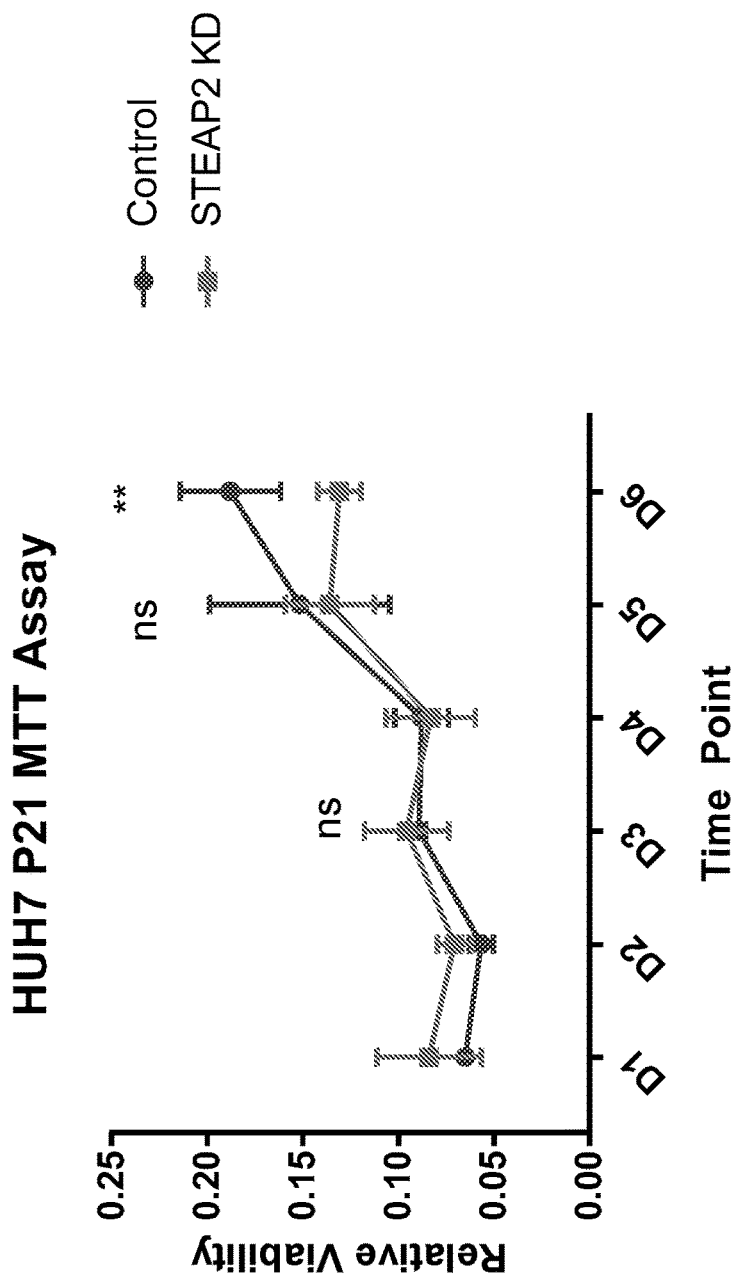
FIG. 6: Knockdown of STEAP2 reduced HUH7 cell viability measured with MTT assay. STEAP2 pool siRNA (25 nM) was used to knockdown STEAP2 in HUH7. Cell viability assay (MTT) was carried out for 6 days. $P<0.005$

Knockdown of STEAP2 reduced viability of HCC cells, which was measured using the MTT assay. Results for HCC SNU398 and HUH7 cells are shown in FIG. 5 and FIG. 6, respectively.

Figure 7:
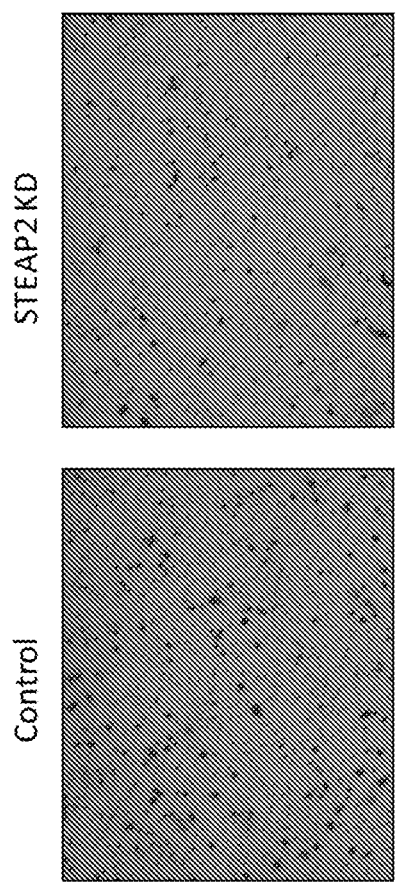
FIG. 7: Knockdown of STEAP2 reduced SNU398 migration. STEAP2 pool siRNA (25 nM) was used to knockdown STEAP2 in SNU398 cells in 60 mm. The cells were then plated in 24-well transwell chambers (Corning Inc., Corning, N.Y., USA) with an 8-μm pore membrane, incubated for 16 hr. For SNU398 P6, we plated 25,000 cells per transwell. $p<0.005$
Figure 7:
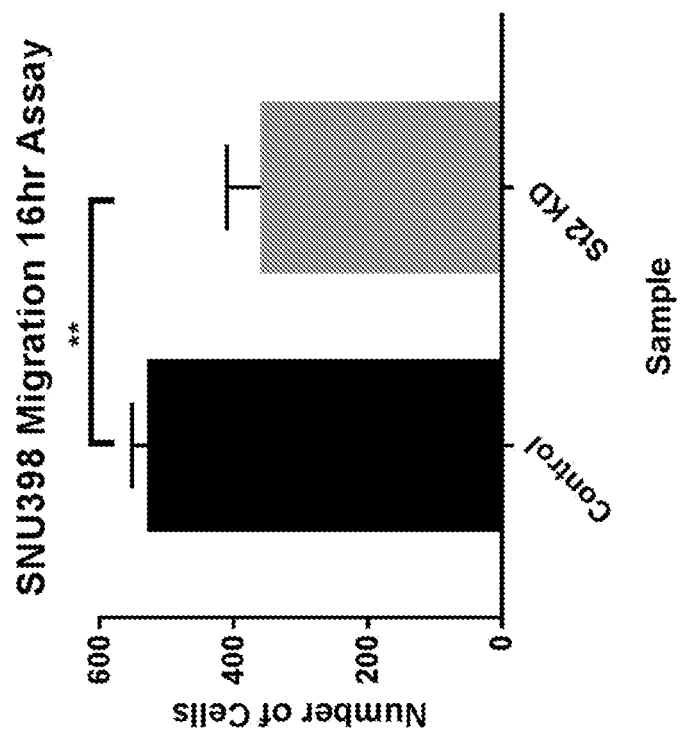
Figure 8:
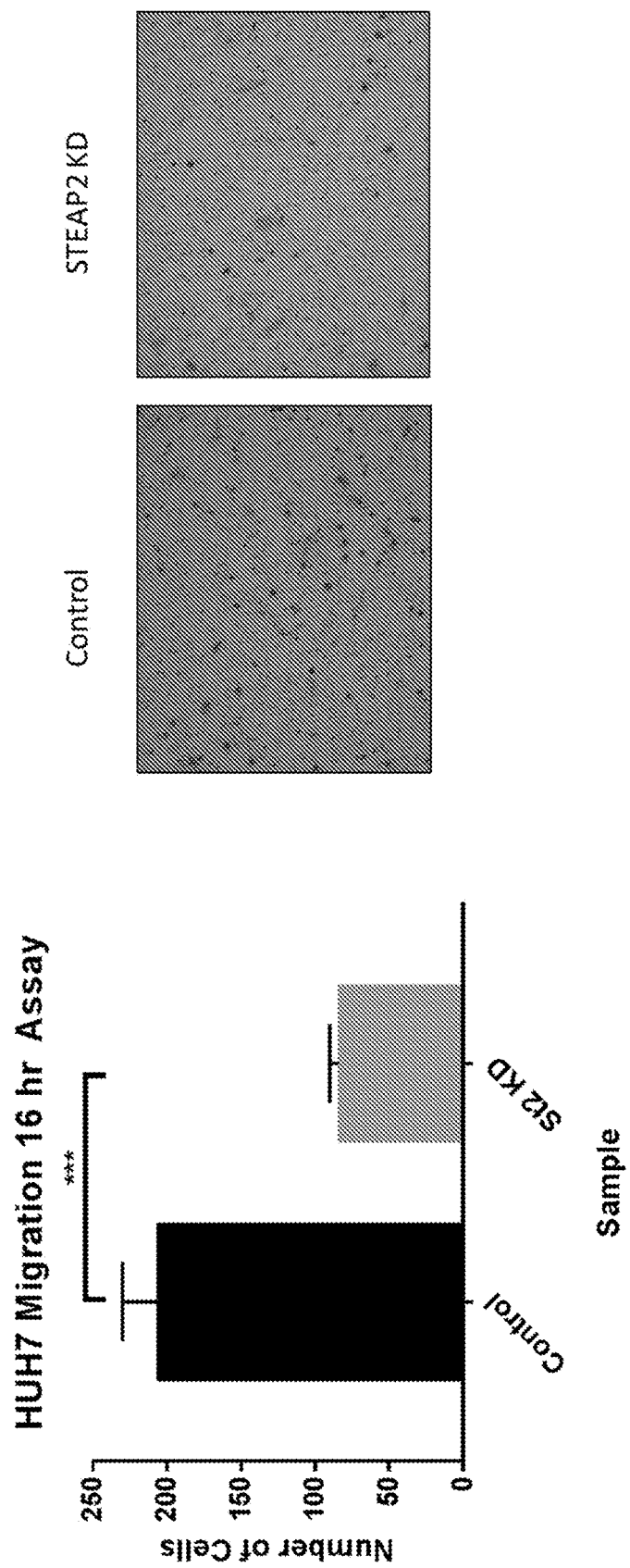
FIG. 8: Knockdown of STEAP2 reduced HUH7 migration. STEAP2 pool siRNA (25 nM) was used to knockdown STEAP2 in HUH7 cells in 60 mm. The cells were then plated in 24-well transwell chambers (Corning Inc., Corning, N.Y., USA) with an 8-μm pore membrane, incubated for 16 hr. For HUH7, we plated 30,000 cells per transwell. $p<0.001$

Knockdown of STEAP2 also reduced migration of HCC cells. Results for reduced migration of SNU398 and HUH7 are shown in FIG. 7 and FIG. 8, respectively.

These data indicate that STEAP2 is specifically overexpressed in HCC tissues, and STEAP2 is also overexpressed in Hispanic HCC in comparison to HCC in non-Hispanic white patients. Without wishing to be bound by any theory, these data support the idea that STEAP2 may promote malignancy in HCC cells by stimulating their proliferation and migration.

Figure 9:
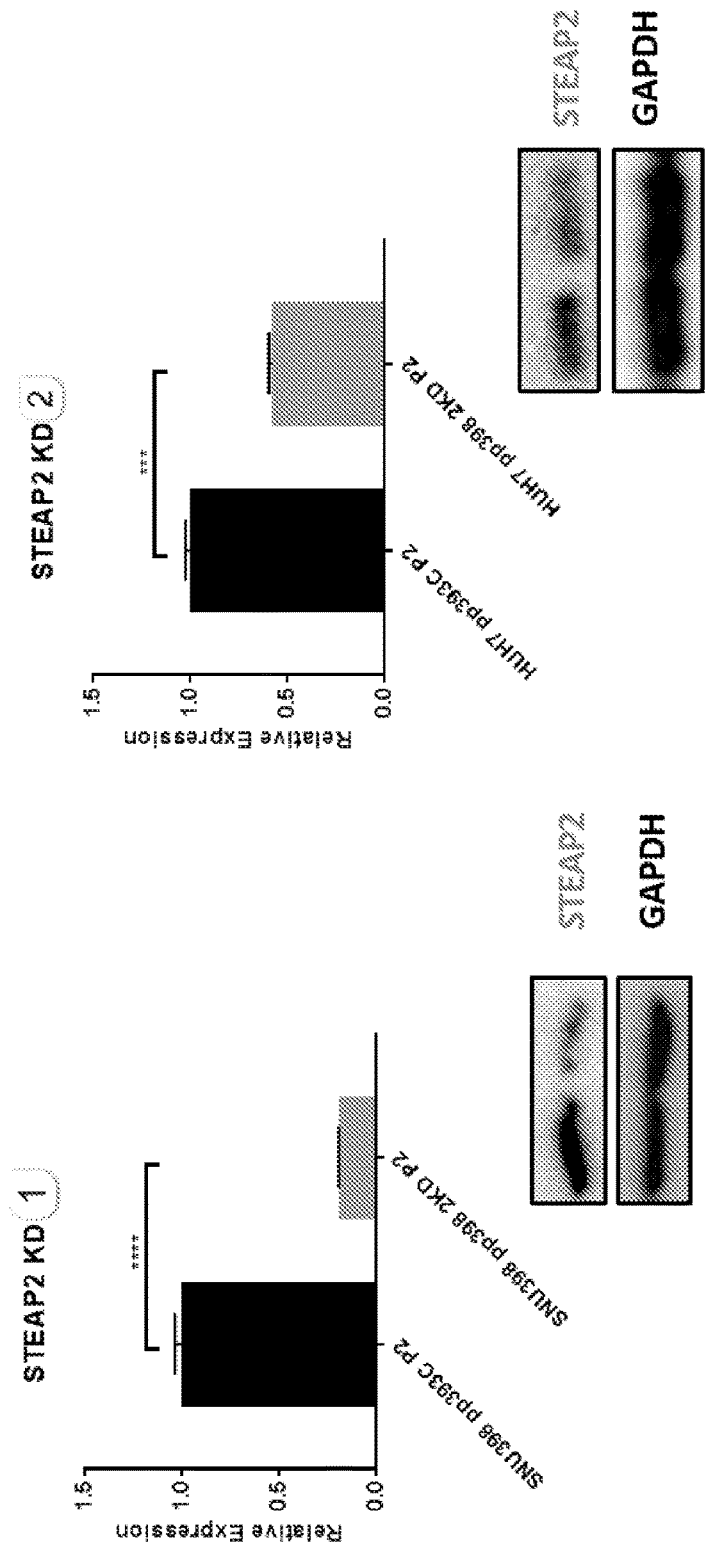
FIG. 9: Stable STEAP2 knockdown in HCC cell lines. The control plasmid (pp393) or the STEAP2-targeting shRNA construct, pp398 were produced and transfected into cells using Lipofectamine® 2000. Stable STEAP2 knockdown was observed in HCC cell lines in multiple HCC cell lines. ***$P<0.0005$. Error bar: SEM.

Additional experiments were performed to stably knockdown STEAP2 in HCC lines. The control plasmid, pp393, is a TRC2-pLKO-puro vector (SHC201 SIGMA). The STEAP2-targeting shRNA construct, pp398, was produced by Sigma-Aldrich (St. Louis, Mo.) and used the following sequence: CCGGGCCAGTGGTGGTAGCTATAAGCTC-GAGCTTATAGCTACCACCACTGGCTTT TTG (SEQ ID NO:1). The plasmids pp393 or pp398 were transfected into HCC cell lines by lentiviral transduction to create STEAP2shRNA expressing cell lines and control cell lines according to the manufacturer's instructions using Lipofectamine® 2000. HCC cell lines, SNU398 and HUH7, stably transfected were selected with 1 ug/ml for HUH7 and 2 ug/ml for SNU398 puromycin after infection with lentivirus. As shown in FIG. 9, stable knockdown of STEAP2 in multiple HCC cell lines was observed.

Figure 10:
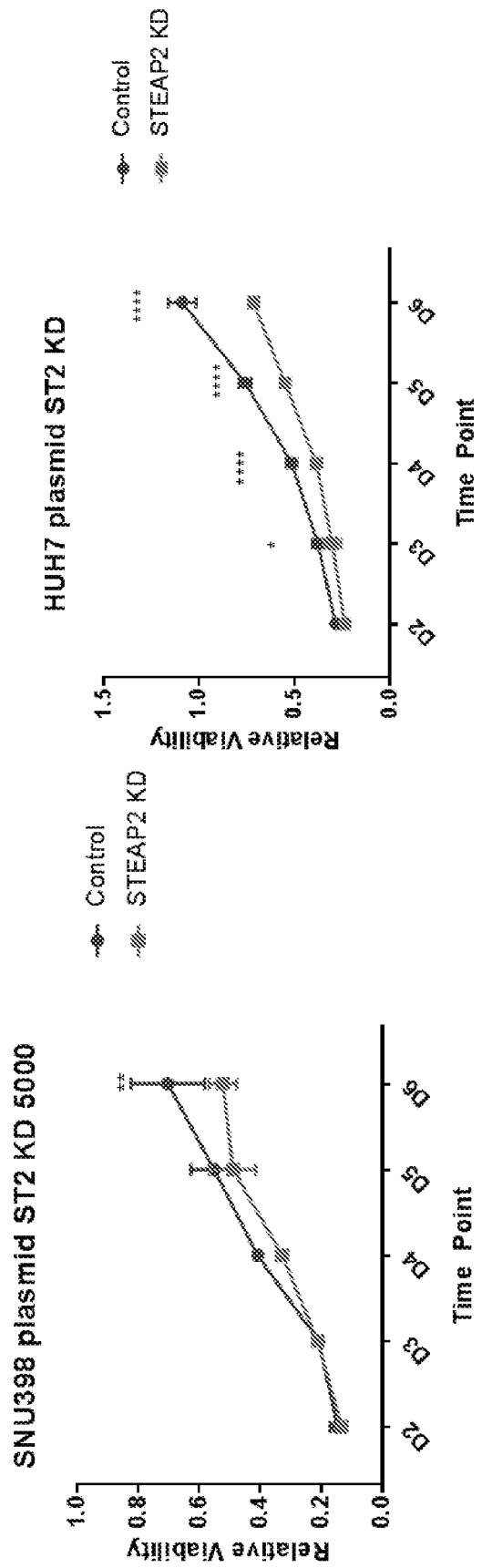
FIG. 10: STEAP2 knockdown decreased proliferation. Stably transfected SNU398 and HUH7 STEAP2shRNA expressing cell lines and control cell lines were utilized for cell viability assay (MTT), which was carried out for 6 days. *$P<0.05$. Error bar: SEM.

STEAP2 knockdown was observed to decrease proliferation of HCC cells. Stably transfected SNU398 and HUH7 STEAP2shRNA expressing cell lines and control cell lines were utilized for cell viability assay (MTT), which was carried out for 6 days. 5000 cells/well for SNU398 and 4000 cells/well for HUH7 were plated. STEAP2 knockdown resulted in a statistically significant decrease in proliferation of HCC cell lines (SNU398 and HUH7). Results are shown in FIG. 10.

Figure 11:
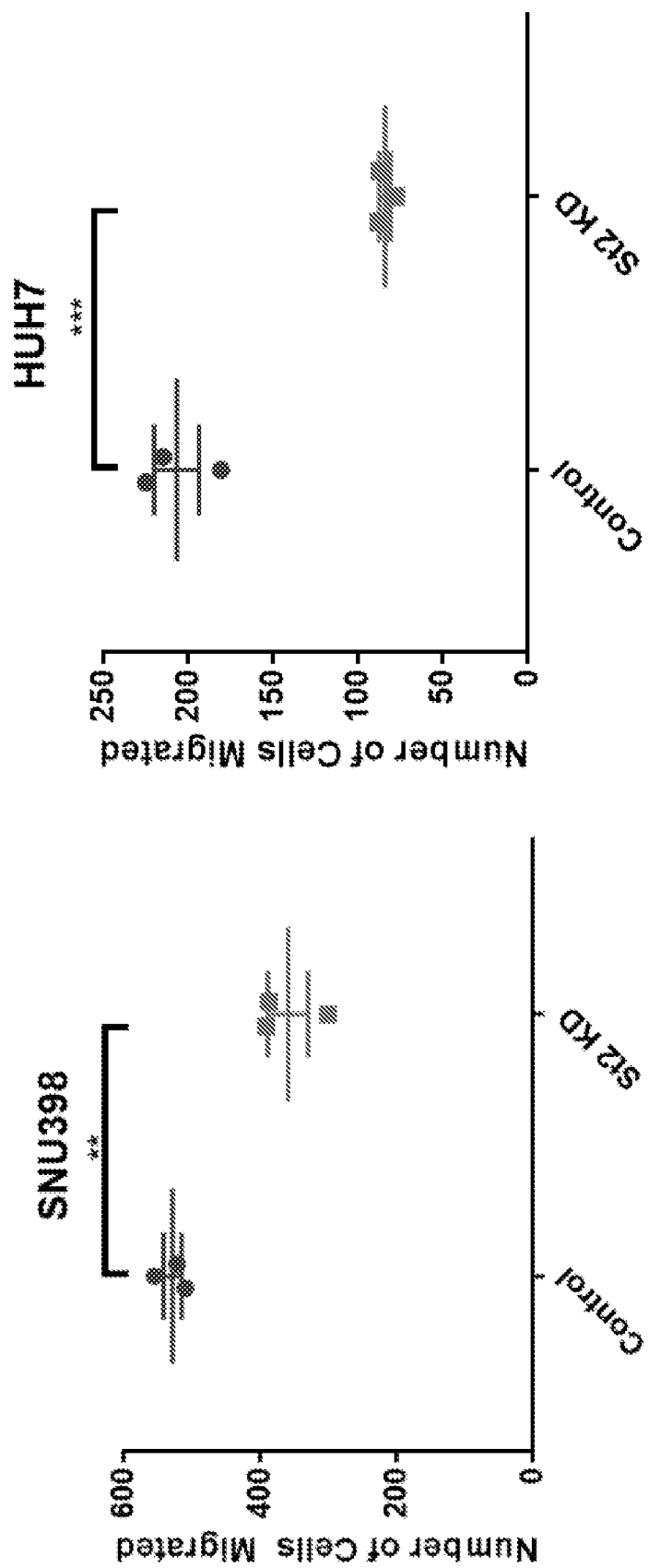
FIG. 11: STEAP2 knockdown decreased cell migration. Stably transfected SNU398 and HUH7 STEAP2shRNA expressing cell lines and control cell lines were utilized for migration assay. **$p<0.006$.

STEAP2 Knockdown was observed to decrease cell migration in HCC cell lines. Stably transfected SNU398 and HUH7 STEAP2shRNA expressing cell lines and control cell lines were utilized for migration assay. The cells were plated in 24-well transwell chambers (Corning Inc., Corning, N.Y., USA) with an 8-μm pore membrane, incubated for 16 hr. For SNU398 P6, we plated 25,000 cells per transwell, and for HUH7 P6, we plated 45,000 cells per transwell. Results are shown in FIG. 11.

Figure 12:
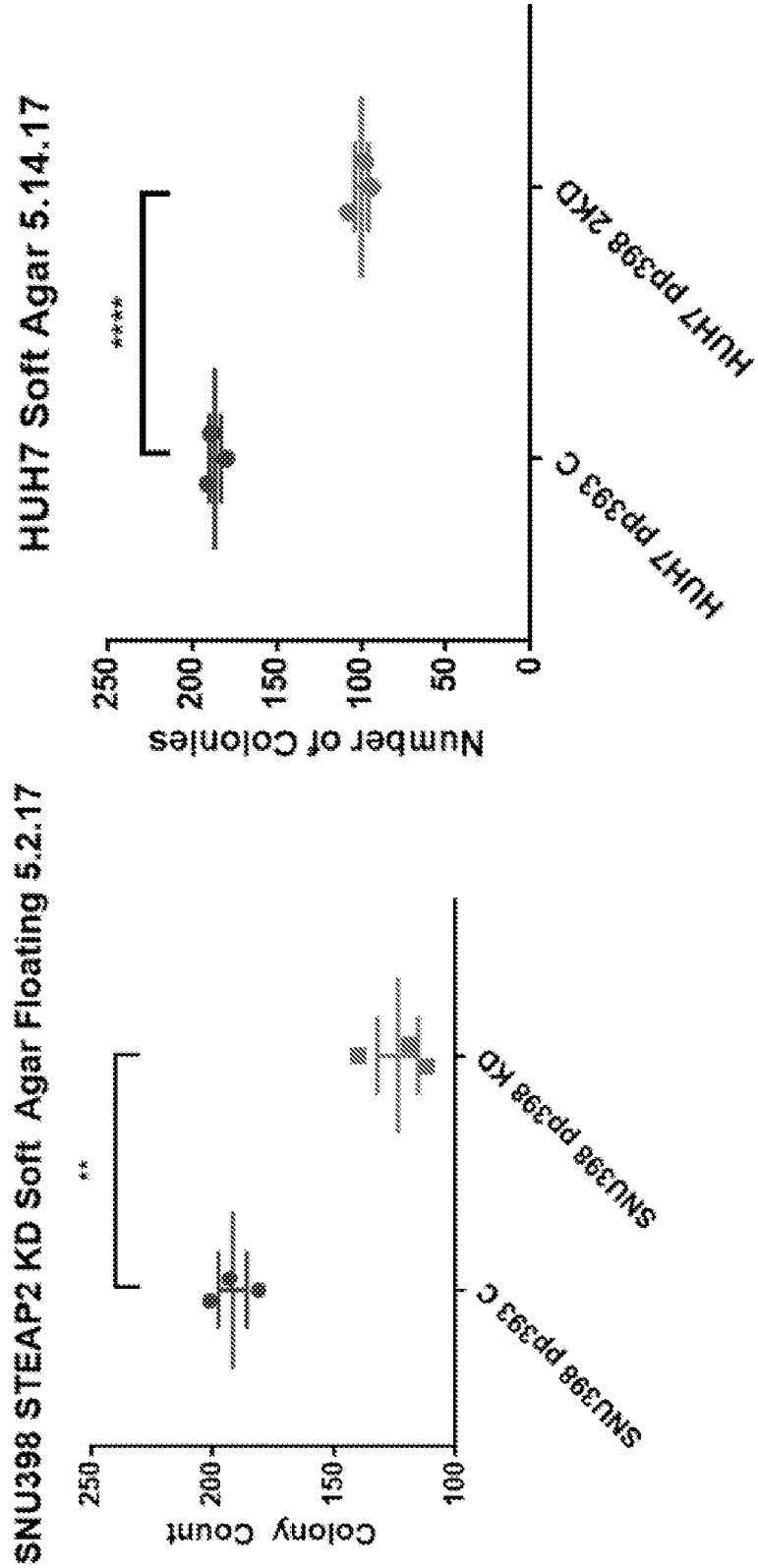
FIG. 12: STEAP2 knockdown decreased anchorage independent growth. Stably transfected SNU398 and HUH7 STEAP2shRNA expressing cell lines and control cell lines were utilized for anchorage independent growth assay. , **$P<0.005$, Error bars: SEM.

STEAP2 knockdown resulted in decreased anchorage independent growth. Stably transfected SNU398 and HUH7 STEAP2shRNA expressing cell lines and control cell lines were utilized for anchorage independent growth assay. The cells were resuspended in 250 ul 0.4% agarose supplemented with 10% FBS, and layered on top of pre-gelled bottom layer composed of 0.8% agarose supplemented with 10% FBS. Final cell number was 3,000 cells/well in 24-well tissue culture plates. SNU398 incubated for 14 days and HUH7 for 16 days. Results are shown in FIG. 12.

Figure 13:
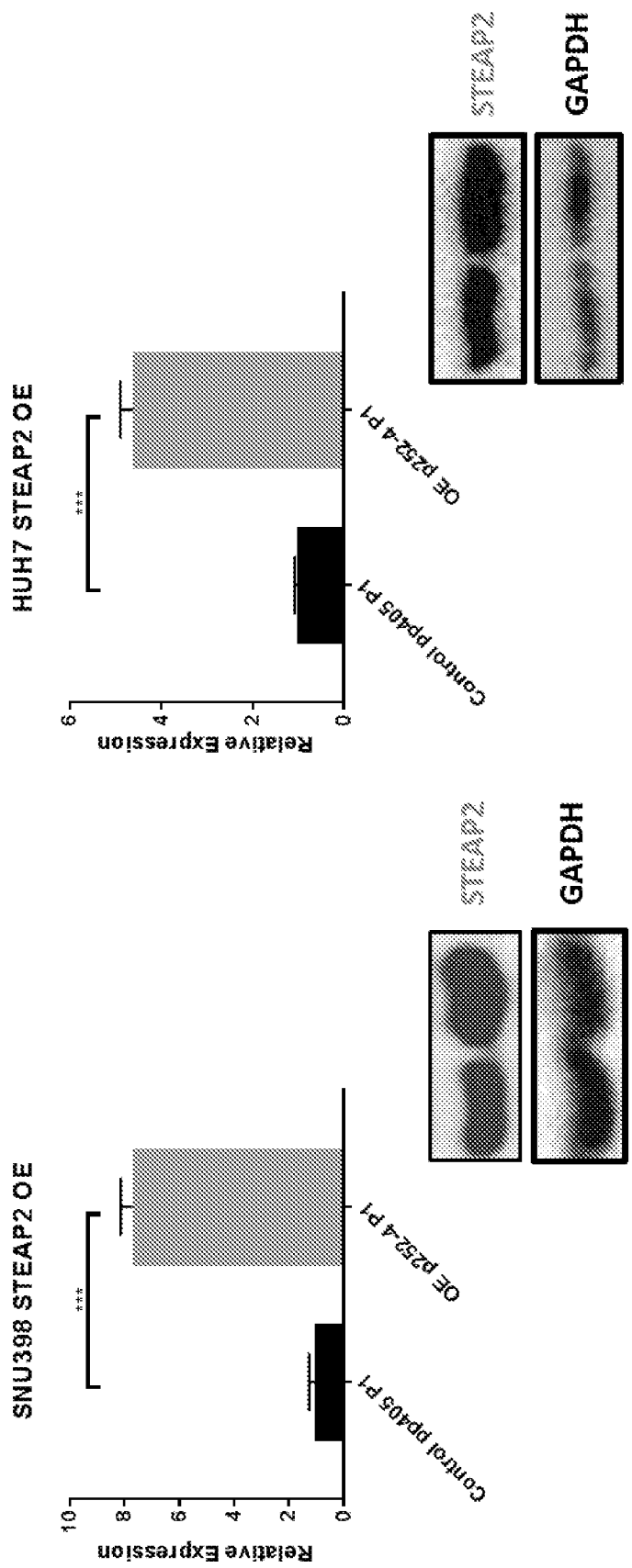
FIG. 13: Stable STEAP2 overexpression in HCC cell lines was observed. Overexpression of STEAP2 mRNA was confirmed by real-time RT-PCR (top panels) and STEAP2 protein by Western blots (bottom panels). ***$P<0.0005$. Error bar: SEM.

The control plasmid, pp405, is a pCDH-CMV-MCS-EF1-copGFP vector (System Biosciences CD511B-1). The STEAP2 overexpression plasmid, p252-4 was made by cutting out the STEAP2 coding sequence from a previously made vector into the control vector pp405; restriction enzymes BamHI and MluI were used to insert the STEAP2 sequence. The plasmids pp405 or p252-4 were transfected into HCC cell lines by lentiviral transduction to create STEAP2 overexpressing cell lines and control cell lines according to the manufacturer's instructions using Lipofectamine 2000. HCC cell lines, SNU398 and HUH7, stably transfected were confirmed to express high fluorescent levels of GFP. Overexpression of STEAP2 mRNA was confirmed by real-time RT-PCR (FIG. 13, top panels), and overexpression of STEAP2 protein was confirmed by Western blot (FIG. 13, bottom panels).

Figure 14:
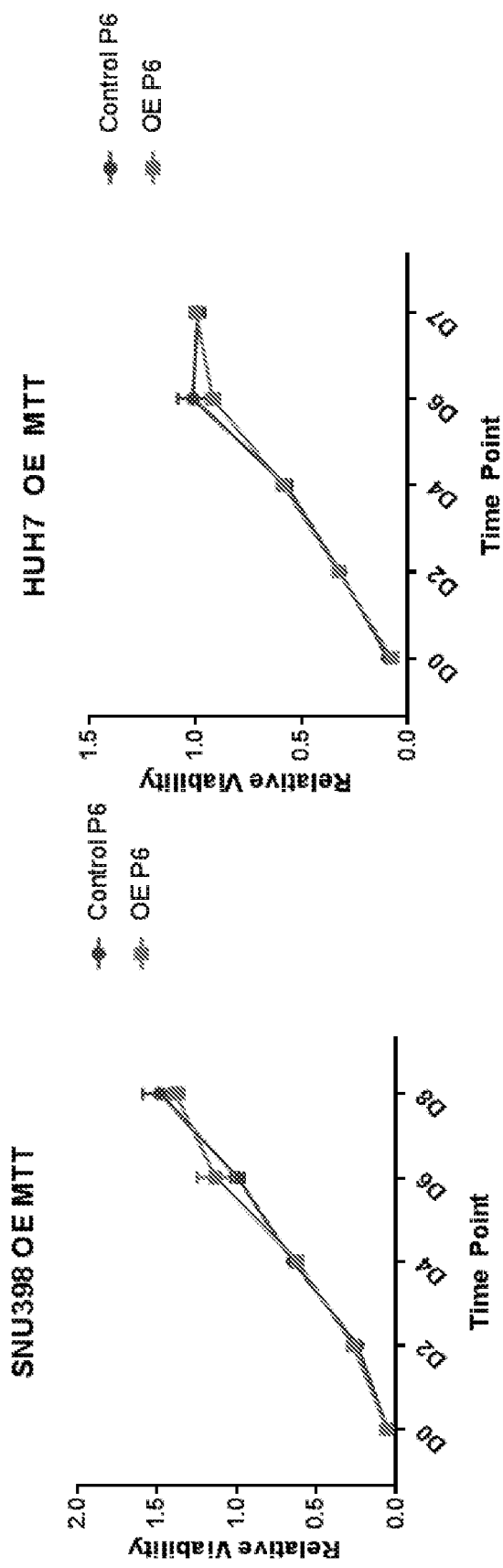
FIG. 14: STEAP2 overexpression did not affect proliferation. Error bar: SEM.

STEAP2 overexpression did not affect proliferation of HCC cell lines. Stably transfected SNU398 and HUH7 STEAP2 overexpressing cell lines and control cell lines were utilized for cell viability assay (MTT), which was carried out for 6-7 days. 5000 cells/well for SNU398 and 4000 cells/well for HUH7 were plated. Results are shown in FIG. 14.

Figure 15:
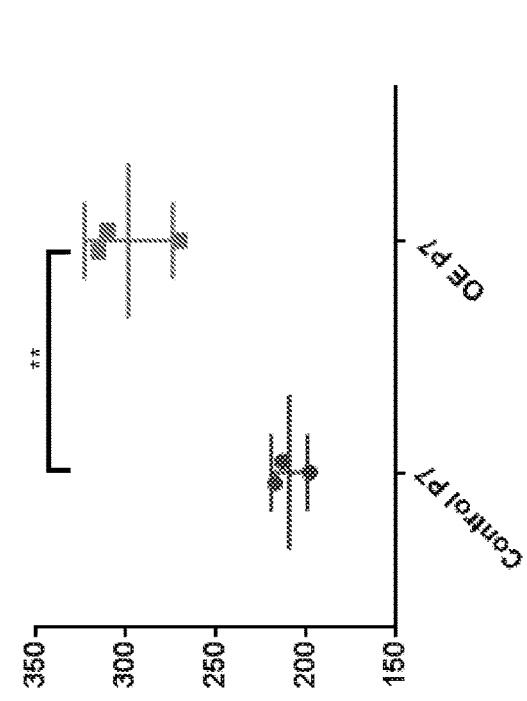
FIG. 15: STEAP2 overexpression increased migration of HCC cell lines. Stably transfected SNU398 and HUH7 STEAP2 overexpressing cell lines and control cell lines were utilized for migration assay. *$p<0.01$. **, $P<0.05$. Error bar: SEM.
Figure 15:
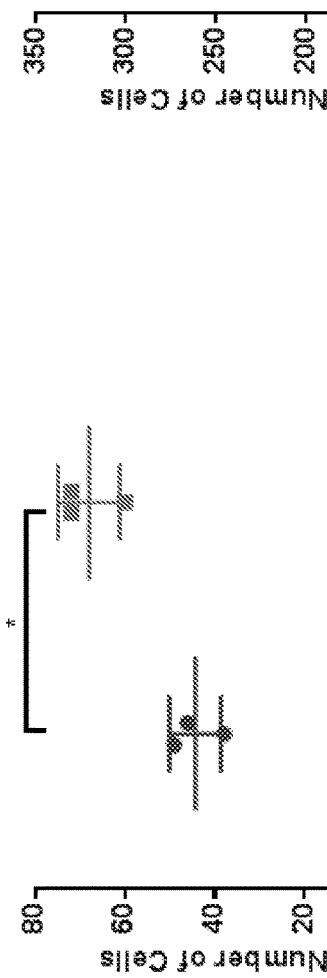
Figure 15:

STEAP2 overexpression increased migration of HCC cell lines. Stably transfected SNU398 and HUH7 STEAP2 overexpressing cell lines and control cell lines were utilized for migration assay. The cells were plated in 24-well transwell chambers (Corning Inc., Corning, N.Y., USA) with an 8-μm pore membrane, incubated for 16 hr. For SNU398 P6, we plated 25,000 cells per transwell, and for HUH7 P6, we plated 45,000 cells per transwell. Results are shown in FIG. 15.

Figure 16:
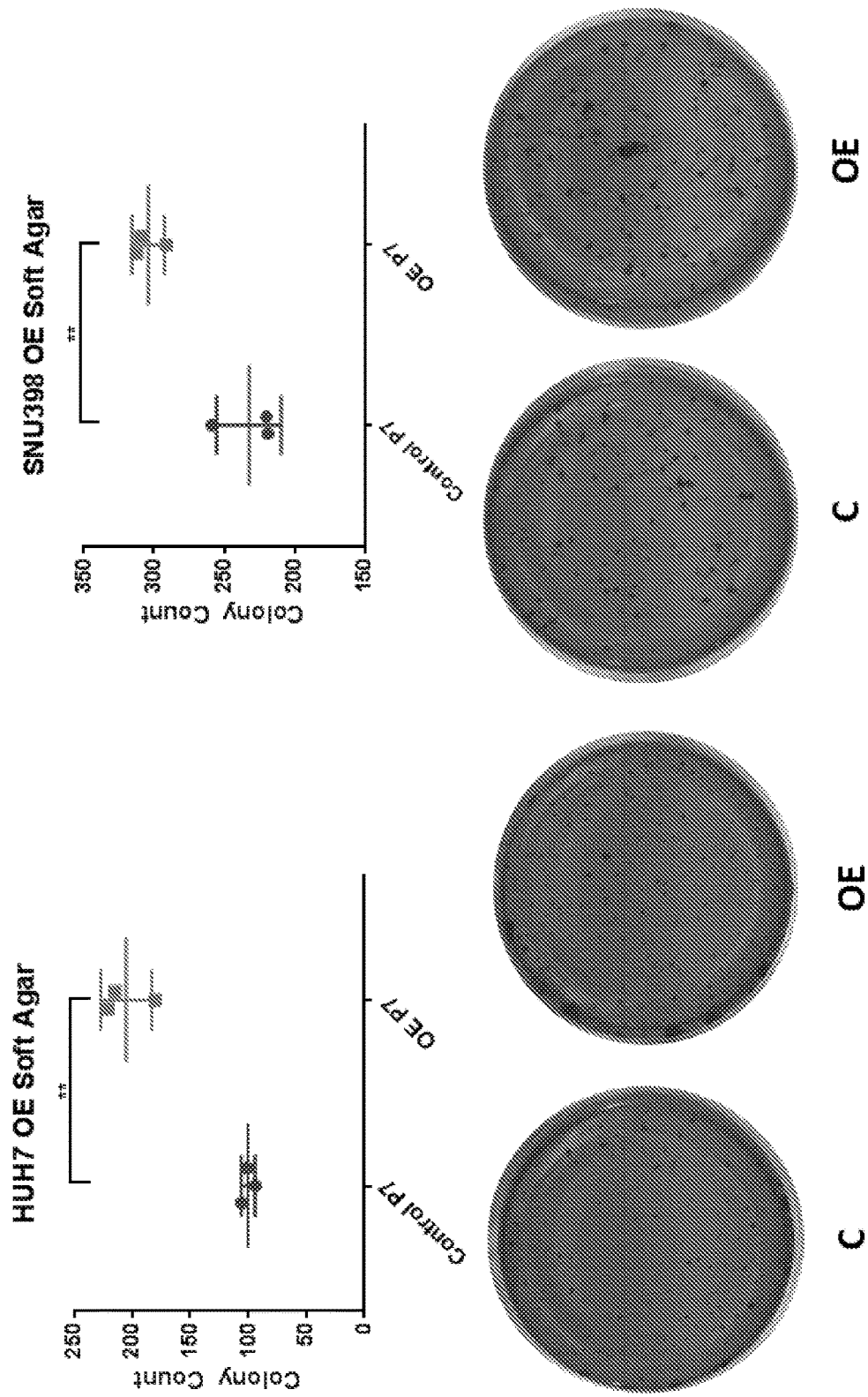
FIG. 16: STEAP2 Overexpression increased soft agar colony formation. Stably transfected SNU398 and STEAP2 overexpressing cell lines and control cell lines were utilized for anchorage independent growth assay. **P<0.05. Error bar: SEM.

STEAP2 Overexpression increased soft agar colony formation. Stably transfected SNU398 and STEAP2 overexpressing cell lines and control cell lines were utilized for anchorage independent growth assay. The cells were resuspended in 250 ul 0.4% agarose supplemented with 10% FBS, and layered on top of pre-gelled bottom layer composed of 0.8% agarose supplemented with 10% FBS. Final cell number was 3,000 cells/well in 24-well tissue culture plates. SNU398 incubated for 14 days and HUH7 for 16 days. Results are shown in FIG. 16.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,797,368
U.S. Pat. No. 4,816,567
U.S. Pat. No. 5,034,506
U.S. Pat. No. 5,139,941
U.S. Pat. No. 5,235,033
U.S. Pat. No. 6,268,490
U.S. Pat. No. 6,506,559
U.S. Pat. No. 6,569,620
U.S. Pat. No. 6,573,099
U.S. Pat. No. 6,673,611
U.S. Pat. No. 6,716,580
U.S. Pat. No. 6,770,748
U.S. Pat. No. 6,806,084
U.S. Pat. No. 8,734,853
U.S. Pat. No. 8,895,717
U.S. Patent Publication No. 2002/0115080
U.S. Patent Publication No. 2002/0168707
U.S. Patent Publication No. 2003/0051263
U.S. Patent Publication No. 2003/0055020
U.S. Patent Publication No. 2003/0159161
U.S. Patent Publication No. 2004/0019001
U.S. Patent Publication No. 2004/0064842
U.S. Patent Publication No. 2004/0265839
U.S. Patent Publication No. 2005/0014166
U.S. Patent Publication No. 2005/0107325
U.S. Patent Publication No. 2005/0182005
Ding and Cantor, *Proc. Natl. Acad. Sci. USA,* 100:3059-3064, 2003.
Ferguson et al., *Proc. Natl. Acad. Sci. USA,* 97(11):6049-6054, 2000.
Fukumura et al., *Nucl. Acids. Res.,* 31(16):e94, 2003.
Godfrey et al., *J. Molec. Diagn.,* 2: 84-91, 2000.
Kawamoto et al., *Genome Res.,* 12:1305-1312, 1999.
Korkmaz et al., "Molecular cloning and characterization of STAMP1, a highly prostate specific six transmembrane protein that is overexpressed in prostate cancer." *J Biol Chem* 277:36689-96, 2002.
Krutzfeldt et al., *Nature,* 438(7068):685-689, 2005.
Liang and Pardee, *Science,* 257:967-971, 1992.
Llovet et al. "The Barcelona approach: diagnosis, staging, and treatment of hepatocellular carcinoma." *Liver Transpl.;* 10(2 Suppl 1):S115-20. Review, February 2004.
Oliphant et al., In: *Discovery of Markers for Disease* (Supplement to Biotechniques), June 2002.
Parker and Barnes, *Methods Mol Biol.,* 106:247-83, 1999.
Porkka et al. "Cloning and characterization of a novel six-transmembrane protein STEAP2, expressed in normal and malignant prostate." *Lab Invest* 82:1573-82, 2002.
Simonetti et al., Treatment of hepatocellular carcinoma: a systematic review of randomized controlled trials. *Ann Oncol.,* 8(2):117-36, 1997.
Song et al., *Nat Med* 9(3):347-51, 2003.
Soutschek et al., *Nature,* 432(7014):173-178, 2004.
Specht et. al., *Am. J. Pathol.,* 158: 419-29, 2001.
Velculescu et al., *Cell,* 88:243-51, 1997.
Velculescu et al., *Science,* 270:484-487, 1995.
Wadhwa et al., *Curr. Opin. Mol. Ther.,* 6(4):367-372, 2004.
Weis et al., *Trends in Genetics,* 8:263 264, 1992.
Yang et al., *Genome Res.,* 11:1888-1898, 2001.

What is claimed is:

1. A method of treating a liver cancer in a mammalian subject comprising administering a therapeutically effective amount of a six-transmembrane epithelial antigen of prostate 2 (STEAP2) inhibitor to the subject;
   wherein the STEAP2 inhibitor is an inhibitory nucleic acid; and
   wherein the liver cancer is hepatocellular carcinoma (HCC).

2. The method of claim 1, wherein the hepatocellular carcinoma is a fibrolamellar carcinoma.

3. The method of claim 1, wherein the liver cancer is non-metastatic.

4. The method of claim 1, wherein the liver cancer is metastatic.

5. The method of claim 1, wherein the STEAP2 inhibitor is an inhibitory nucleic acid.

6. The method of claim 5, wherein the STEAP2 inhibitor is a small interfering RNA (siRNA), a double-stranded RNA (dsRNAs), a microRNAs (miRNA), or a short hairpin RNAs (shRNA).

7. The method of claim 6, wherein the STEAP2 inhibitor is a siRNA.

8. The method of claim 5, wherein the nucleic acid has been chemically modified to reduce degradation or contains one or more chemically modified nucleic acid analogs.

9. The method of claim 7, wherein the nucleic acid is a locked nucleic acid (LNA).

10. The method of claim 5, wherein the inhibitory nucleic acid is comprised in liposomes or nanoparticles.

11. The method of claim 10, wherein the liposomes are neutral liposomes or cationic liposomes.

12. The method of claim 10, wherein the liposomes comprise a phosphatidylcholine, a phosphatidylethanolamine phospholipid, DOTAP, cholesterol, or chitosan.

13. The method of claim 7, wherein the siRNA comprises siRNA J-010739-09 (CAACAAUAUUCAAGCGCGA; SEQ ID NO:2), siRNA J-010739-10 (AGUCUUAAUCC-UAUGCAAA; SEQ ID NO:3), siRNA J-010739-11 (GGCCAGAUGAGCUAAAUUA; SEQ ID NO:4), siRNA J-010739-12 (ACAAGUAUGCUGUCAAAUU; SEQ ID NO:5), or STEAP2 shRNA (CCGGGCCAGTGGT- GGTA-GCTATAAGCTCGAGCTTATAGCTACCACCACTGGC-TTTTT G; SEQ ID NO:1).

14. The method of claim 1, wherein the subject is a human.

15. The method of claim 14, wherein the subject is Caucasian.

16. The method of claim 14, wherein the subject is Hispanic.

17. The method of claim 1, wherein the STEAP2 inhibitor is administered parenterally, intravenously, intra-hepatic portal vein, intramuscularly, intraperitoneally, or intra-tumorally.

18. The method of claim 1, wherein the method further comprises administering a second anti-cancer therapy to the subject.

19. The method of claim 18, wherein the second anti-cancer therapy is a surgery, a chemotherapy, an immunotherapy, a liver resection, cryoablation, percutaneous ethanol injection, radiofrequency ablation, transarterial chemoembolization, radiotherapy, radiation therapy, radioembolization, a molecularly targeted therapy, a hormone therapy, a gene therapy, metal ion therapy, or a diet therapy.

* * * * *